United States Patent [19]

Broadhurst et al.

[11] Patent Number: 5,447,929
[45] Date of Patent: Sep. 5, 1995

[54] METHOD OF TREATING JOINT DISORDERS USING HYDROXAMIC DERIVATIVES

[75] Inventors: Michael J. Broadhurst, Barley; Paul A. Brown; William H. Johnson; Geoffrey Lawton, all of Hitchin, England

[73] Assignee: Hoffmann-La Roche Inc., Nutley, N.J.

[21] Appl. No.: 214,895

[22] Filed: Mar. 17, 1994

Related U.S. Application Data

[62] Division of Ser. No. 66,832, May 24, 1993, Pat. No. 5,318,964.

[30] Foreign Application Priority Data

Jun. 11, 1992 [GB] United Kingdom ............ 9212421
Mar. 19, 1993 [GB] United Kingdom ............ 9305720

[51] Int. Cl.⁶ .................... A61K 31/535; A61K 31/54
[52] U.S. Cl. ........................... 514/228.2; 514/212; 514/227.8; 514/235.2; 514/253; 514/323; 514/326; 514/230.5; 514/417; 514/236.2; 514/235.8; 514/235.5
[58] Field of Search ............ 514/228.2, 235.2, 253, 514/323, 326

[56] References Cited

U.S. PATENT DOCUMENTS 4,743,587 5/1988 Dickens et al.

FOREIGN PATENT DOCUMENTS

WOA9005716 5/1990 WIPO.

OTHER PUBLICATIONS

Dayer, et al. Proc. Natl. Acad. Sci. USA(1976), 73,945.
Johnson-Wint. B. Anal. Biochem. (1980) 104, 175.
Handa, et al., Chemical Abstracts, vol. 108, (1988) No. 167,973e.
Broadhurst, et al. Chemical Abstracts, vol. 118, (1993) No. 169,601n.

Primary Examiner—Robert W. Ramsuer
Attorney, Agent, or Firm—George M. Gould; George W. Johnston; Ellen Ciambrone Coletti

[57] ABSTRACT

Hydroxamic acid derivatives of the formula

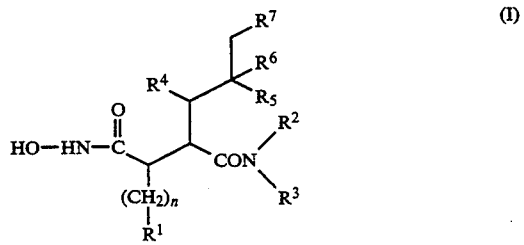

and pharmaceutically acceptable salts thereof, which are collagenase inhibitors useful for the control or prevention of degenerative joint diseases, such as, rheumatoid arthritis and ostecarthritis or for the treatment of invasive tumours, atherosclerosis or multiple sclerosis, are described. Said compounds can be prepared either by hyclroxamidating a corresponding carboxylic acid or deprotecting a corresponding benzyloxycarbamoyl compound.

9 Claims, No Drawings

METHOD OF TREATING JOINT DISORDERS USING HYDROXAMIC DERIVATIVES

This is a division, of application Ser. No. 08/066,832 filed May 24, 1993 now U.S. Pat. No. 5,318,964.

BRIEF SUMMARY OF THE INVENTION

The invention relates to hydroxamic acid derivatives.

The hydroxamic acid derivatives provided by the present invention are compounds of the formula

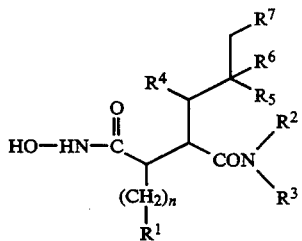

wherein $R^1$ is a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other C atoms by lower alkyl or oxo and/or on any additional N atom(s) by lower alkyl or aryl;

$R^2$ is lower alkyl and $R^3$ is lower alkyl or aryl, or $NR^2R^3$ is a saturated 5-, 6- or 7-membered heterocyclic ring which optionally contains $-NR^a$, $-O-$, $-S-$, $-SO-$ or $-SO_2-$ as a ring member and/or which is optionally substituted by hydroxy, lower alkoxy, oxo, ketalized oxo, amino, mono(-lower alkyl)amino, di(lower alkyl)amino, carboxy, lower alkoxycarbonyl, hydroxy-methyl, lower alkoxymethyl, carbamoyl, mono(lower alkyl)-carbamoyl, di(lower alkyl)carbamoyl or hydroxyimino;

$R^a$ is hydrogen, lower alkyl, lower alkanoyl, aryl-loweralkanoyl, lower alkoxycarbonyl, aryl-lower alkoxycarbonyl or mono(lower alkyl)carbamoyl;

$R^4$, $R^5$, $R^6$ and $R^7$ each, independently, is hydrogen or methyl, provided that at least two of these symbols are hydrogen; and n stands for 1-4; and pharmaceutically acceptable salts thereof.

DETAILED DESCRIPTION OF THE INVENTION

The hydroxamic acid derivatives provided by the invention are compounds of the formula

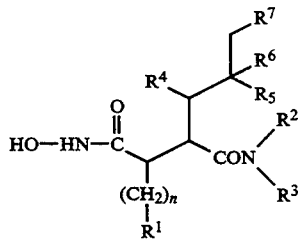

wherein $R^1$ is a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other C atoms by lower alkyl or oxo and/or on any additional N atom(s) by lower alkyl or aryl;

$R^2$ is lower alkyl and $R^3$ is lower alkyl or aryl, or $NR^2R^3$ is a saturated 5-, 6- or 7-membered heterocyclic ring which optionally contains $-NR^a$, $-O-$, $-S-$, $-SO-$ or $-SO_2-$ as a ring member and/or which is optionally substituted by hydroxy, lower alkoxy, oxo, ketalized oxo, amino, mono(-lower alkyl)amino, di(lower alkyl)amino, carboxy, lower alkoxycarbonyl, hydroxy-methyl, lower alkoxymethyl, carbamoyl, mono(lower alkyl)-carbamoyl, di(lower alkyl)carbamoyl or hydroxyimino;

$R^a$ is hydrogen, lower alkyl, lower alkanoyl, aryl-loweralkanoyl, lower alkoxycarbonyl, aryl-lower alkoxycarbonyl or mono(lower alkyl)carbamoyl;

$R^4$, $R^5$, $R^6$ and $R^7$ each, independently, is hydrogen or methyl, provided that at least two of these symbols are hydrogen; and n stands for 1-4; and pharmaceutically acceptable salts thereof.

The compounds of formula I possess valuable pharmacological properties. In particular, they are collagenase inhibitors and can be used in the control or prevention of degenerative joint diseases, such as, rheumatoid arthritis and osteoarthritis or in the treatment of invasive tumors, atherosclerosis or multiple sclerosis.

Objects of the present invention are the compounds of formula I and their pharmaceutically acceptable salts as well as their use as therapeutically active substances; a process for the preparation of said compounds and salts; intermediates useful in said process; medicaments containing said compounds and salts and the preparation of these medicaments; and the use of said compounds and salts in the control or prevention of illnesses or in the improvement of health, especially in the control or prevention of degenerative joint diseases or in the treatment of invasive tumors or atherosclerosis, or for the preparation of a medicament for the control or prevention of degenerative joint diseases or for the treatment of invasive tumors, atherosclerosis or multiple sclerosis.

As used in this Specification, the term "lower alkyl", alone or in combination, shall mean a straight-chain or branched-chain alkyl group containing a maximum of six, preferably one to four carbon atoms, such as, methyl, ethyl, n-propyl, isopropyl, n-butyl, sec.butyl, isobutyl, tert.butyl, n-pentyl, n-hexyl and the like. The term "lower alkoxy", alone or in combination, shall mean a straight-chain or branched-chain alkoxy group, containing a maximum of six, preferably one to four carbon atoms, such as, methoxy, ethoxy, n-propoxy, isopropoxy, n-butoxy, tert.butoxy and the like. The term "aryl" shall mean phenyl which is optionally substituted by, for example, lower alkyl, lower alkoxy and-/or halogen, i.e. fluorine, chlorine, bromine or iodine. The term "lower alkanoyl", alone or in combination, shall mean an acyl group derived from an alkanoic acid containing up to six carbon atoms, for example, acetyl, propionyl, butyryl, isobutyryl and the like. A ketalized oxo group can be, for example, ethylenedioxy.

The compounds of formula I form pharmaceutically acceptable salts with bases, for example, alkali metal hydroxides, such as, sodium hydroxide and potassium hydroxide, alkaline earth metal hydroxides, such as, calcium hydroxide and magnesium hydroxide, ammonium hydroxide and the like. The compounds of formula I which are basic form pharmaceutically acceptable salts with acids. As such salts, there come into consideration not only salts with inorganic acids, for example, hydrohalic acids, such as, hydrochloric acid and hydrobromic acid, sulfuric acid, nitric acid, phosphoric acid and the like, but also salts with organic acids such as acetic acid, tartaric acid, succinic acid, fumaric acid, maleic acid, malic acid, salicylic acid, citric acid, methanesulfonic acid, p-toluenesulfonic acid etc.

The compounds of formula I contain at least two asymmetric carbon atoms and can accordingly exist as optically active enantiomers, as diastereoisomers or as racemates. The invention is intended to embrace all of these forms.

Compounds of formula I in which the N-heterocyclic ring $R^1$ optionally contains as additional hetero atom(s-)one or two N atoms, one N atom and one O atom or one O atom, are preferred. Especially preferred rings denoted by $R^1$ are those of the formulas:

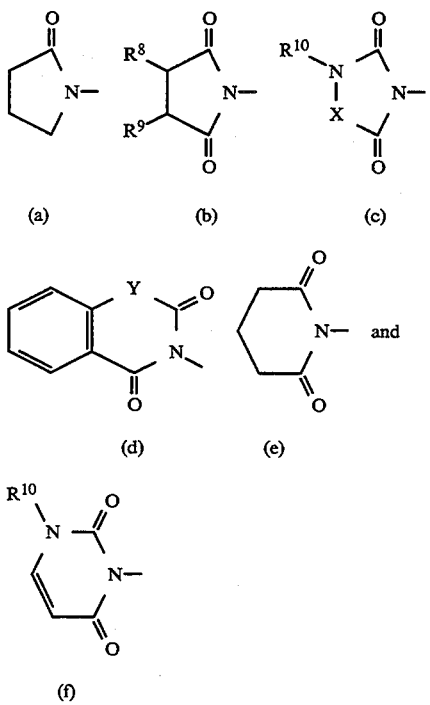

in which

R$^8$ and R$^9$ each, independently, is hydrogen or taken together are an additional bond or the remainder of a fused benzene ring;

R$^{10}$ is hydrogen, lower alkyl or aryl;

X is —CO—, —CH$_2$—, —CH(lower alkyl)—, —C(-lower alkyl)$_2$—, —NH—, —N(lower alkyl)— or —O—; and Y is —O—, —NH— or —N(lower alkyl)—. Examples of such rings are 2-oxo-1-pyrrolidinyl, 2,5-dioxo-1-pyrrolidino, phthalimido, 1,2-dimethyl-3,5-dioxo- 1,2,4-triazolidin-4-yl, 3-methyl-2,5-dioxo-1-imidazolidinyl, 3,4,4-trimethyl-2,5- dioxo-1-imidazolidinyl, 2-methyl-3,5-dioxo-1,2,4-oxadiaxol-4-yl, 3-methyl-2,4,5-trioxo- 1 -imidazolidinyl, 2,5-dioxo-3-phenyl-1-imidazolidinyl and 2,6-dioxopiperidino. Those rings of formulas (b) and (c), especially phthalimido, 1,2-dimethyl-3,5-dioxo-1,2,4-triazolidin-4-yl, 3-methyl-2,5-dioxo-1-imidazolidinyl or 3,4,4-trimethyl-2,5-dioxo-1-imidazolidinyl, are particularly preferred.

Compounds of formula I in which NR$^2$R$^3$ is a 5-, 6- or 7-membered saturated heterocyclic ring, as described earlier, are preferred. Such rings include 1-pyrrolidinyl, piperidino, 1-piperazinyl, 4-methyl-1 -piperazinyl, hexahydro-1 -pyridazinyl, morpholino, tetrahydro-1,4-thiazin-4-yl, tetrahydro-1,4-thiazin-4-yl 1-oxide, tetrahydro-1,4-thiazin-4-yl 1,1-dioxide and octahydro-1-azocinyl which can be substituted in the manner given earlier; for example, 2-(methylcarbamoyl)-1-pyrrolidinyl, 2-(hydroxymethyl)- 1 -pyrrolidinyl, 4-hydroxylpiperidino, 2-(methylcarbamoyl)piperidino, 4-hydroxyiminopiperidino, 4-methoxypiperidino, 1,4-dioxa-8-azaspiro-[4.5]decan-8-yl, hexahydro-3-(methylcarbamoyl)o2-pyridazinyl and hexahydro-1-(benzyloxycarbonyl)-2-pyridazinyl. Compounds of formula I in which NR$^2$R$^3$ is a 6-membered saturated heterocyclic ring, particularly, morpholino, tetrahydro-1,4-thiazin-4-yl, 4-hydroxypiperidino or hexahydro-3-(methylcarbamoyl-2-pyridazinyl, are especially preferred.

Compounds of formula I in which R$^4$, R$^5$ and R$^7$ each, independently, is hydrogen and R6 is methyl, are also preferred.

Further, compounds of formula I in which n stands for 1 or 2 are preferred.

The most preferred compounds of formula I are:
4-[2(R)-[1(R or S)-(hydroxycarbamoyl)-2-phthalimido-ethyl]-4-methylvaleryl]morpholine;
4-[2(R)-[1 (R or S)-(hydroxycarbamoyl)-2-phthalimido-ethyl]-4-methylvaleryl]tetrahydro-1,4-thiazine;
1-[2(R)-[1(R or S)-(hydroxycarbamoyl)-2-phthalimido-ethyl]-4-methylvaleryl]-4-piperidinol;
1-[2(R)-[1(R or S)-(hydroxycarbamoyl)-2-(1,2-dimethyl-3,5-dioxo-1,2,4-triazolidin-4yl) ethyl]-4-methylvaleryl]-piperidine;
4-[2(R)-[1(R or S)-(hydroxycarbamoyl)-2-(3-methyl-2,5-dioxo-1-imidazolidinyl) ethyl]-4-methylvaleryl]tetrahydro- 1,4-thiazine;
hexahydro-2-[2(R)-[1(R or S)-(hydroxycarbamoyl)-2-phthalimidoethyl]-4-methylvaleryl]-N-methyl-3(S)-pyridazinecarboxamide; and
1-[2(R)-[1(R or S)-(hydroxycarbamoyl)-2-(3,4,4-trimethyl-2,5-dioxo-1-imidazolidinyl) ethyl]-4-methylvaleryl]-4piperidinol.

According to the process provided by the invention, the compounds of formula I and their pharmaceutically acceptable salts can be prepared by (a) reacting an acid of the formula

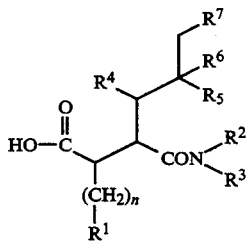

(II)

wherein $R^1$, $R^2$, $R^3$, $R^4$, $R^5$, $R^6$, $R^7$ and n have the significance given earlier, with a compound of the formula $$H_2N\text{-}OZ \qquad (III)$$

wherein Z is hydrogen, tri(lower alkyl)silyl or diphenyl(lower alkyl)silyl, and, where required, cleaving off any diphenyl(lower alkyl)silyl group in the reaction product, or (b) catalytically hydrogenating a compound of the formula

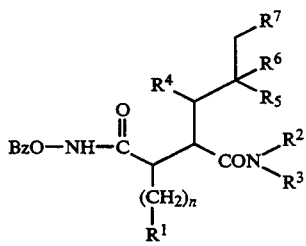

(IV)

wherein $R^1$, $R^2$, $R^3$, $R^4$, $R^5$, $R^6$, $R^7$ and n have the significance given earlier and Bz is benzyl, and, if desired, converting a compound of formula I obtained into a pharmaceutically acceptable salt.

The reaction of an acid of formula II with a compound of formula III, in accordance with embodiment (a) of the process, can be carried out in a known manner, for example, in an inert organic solvent, such as, dimethylformamide or the like, using hydroxybenzotriazole in the presence of a condensation agent, such as, 1-ethyl-3-(3-dimethylaminopropyl)carbodiimide hydrochloride at about 0° C. to about room temperature. Preferred compounds of formula III are those in which Z is hydrogen, tert.butyl-dimethylsilyl or tert.butyldiphenylsilyl. When a compound of formula III, in which Z is tri(lower alkyl)silyl, is used, this group is cleaved during the reaction and working-up, and a compound of formula I is obtained directly. On the other hand, when a compound of formula III, in which Z is diaryl-(lower alkyl)silyl, is used, this group remains in the reaction product and must subsequently be cleaved in a known manner, for example, by means of fluoride ions.

The catalytic hydrogenation of a compound of formula IV, in accordance with embodiment (b) of the process, can be carried out in a known manner; for example, in an inert organic solvent using hydrogen in the presence of a noble metal catalyst. Suitable inert organic solvents are, for example, lower alka, nols, such as, methanol, ethanol, and the like. With respect to the catalyst, this can be, for example, a platinum, palladium or rhodium catalyst which can be supported on a suitable carrier material. Palladium-on-charcoal is the preferred catalyst. The temperature and pressure are not critical, although for convenience the catalytic hydrogenation is preferably carried out at room temperature and under atmospheric pressure.

Acidic compounds of formula I can be converted into pharmaceutically acceptable salts by treatment with bases, and basic compounds of formula I can be converted into pharmaceutically acceptable salts by treatment with acids. Such treatments can be carried out in a conventional manner.

The acids of formula II which are used as starting materials in embodiment (a) of the process also form part of the present invention.

The acids of formula II can be prepared, for example, as illustrated in the following Reaction Scheme in which $R^1$, $R^2$, $R^3$, $R^4$, $R^5$, $R^6$, $R^7$, Bz and n have the significance given earlier and tBu is tert.butyl.

Reaction Scheme

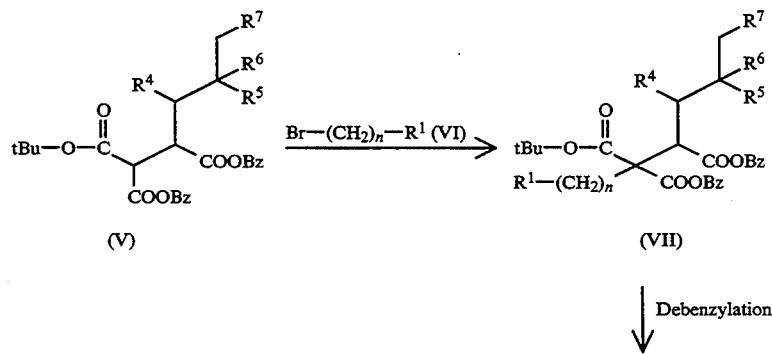

Reaction Scheme -continued

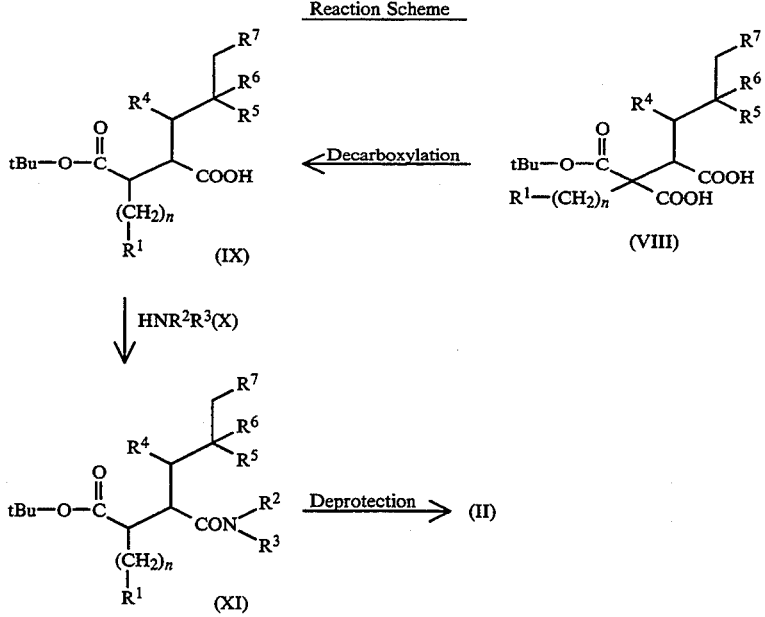

$R^1$–$R^7$, Bz, Br, t-Bu and n are as previously described.

In the foregoing Reaction Scheme, in the first step, an alkanetricarboxylate of formula V is reacted with a bromoalkyl-substituted N-heterocycle of formula VI to give a compound of formula VII. This reaction can be carried out in a generally known manner, for example, by treating the alkane-tricarboxylate in an inert organic solvent, such as, dimethyl-formamide with a strong base, for example, an alkali metal hydride, such as, sodium hydride, subsequently adding the bromoalkyl-substituted N-heterocycle and then allowing the reaction to proceed, preferably at room temperature.

The compound of formula VII obtained is then debenzylated to a compound of formula VIII in a known manner, for example, by hydrogenation in an inert organic solvent, for example, a lower alkanol, such as, methanol or ethanol, in the presence of a catalyst, such as, palladium-on-charcoal.

The subsequent decarboxylation of a compound of formula VIII to a compound of formula IX is also carried out in a known manner, for example, by heating in an aromatic solvent, such as, benzene or toluene, in the presence of a base, such as, N-methylmorpholine.

In the next step a compound of formula IX is reacted with an amine of formula X to give a compound of formula I. This reaction can be carried out in a known manner. For example, the reaction is conveniently carried out in an inert organic solvent, such as, dimethylformamide or the like using hydroxybenzotriazole in the presence of a condensation agent, such as, 1-ethyl-3-(3-dimethylaminopropyl) carbodiimide hydrochloride or by converting the compound of formula IX with oxalyl chloride into the corresponding chloride and reacting this with the amine, expediently in the presence of a base, such as, triethylamine, at about 0°–25° C.

In the final step, a compound of formula XI is deprotected to give a desired acid starting material of formula II. This deprotection can be carried out in a known manner, for example, by treatment with trifluoroacetic acid.

If desired, a compound of formula XI can be functionally modified prior to the deprotection step. Thus, for example, a compound of formula XI in which $NR^2R^3$ is a saturated 5-, 6- or 7-membered membered heterocyclic ring containing —S— as a ring member, can be oxidized in a known manner, for example, using a peracid, such as, m-chloroperbenzoic acid, to a corresponding compound which contains —SO— or —SO$_2$—, as a ring member.

The compounds of formula IV which are used as starting materials in embodiment (b) of the process also form a part of the invention.

The compounds of formula IV can be prepared, for example, by reacting an acid of formula II with O-benzylhydroxylamine. This reaction can be carried out in a known manner, for example, in an inert organic solvent, such as, dimethylformamide, using hydroxybenzotriazole in the presence of a condensation agent, such as, 1-ethyl-3-(3-dimethylaminopropyl)carbodiimide hydrochloride.

The remaining compounds which are used as intermediates or reactants in the preparation of the compounds of formula I are known compounds or analogues of known compounds which can be prepared in a similar manner to the known compounds.

As mentioned earlier, the compounds of formula I and their pharmaceutically acceptable salts are collagenase inhibitors. The in vitro collagenase inhibiting activity of the compounds of formula I and their salts can be demonstrated using collagenase obtained from a culture of human synovial fibroblasts according to the method of Dayer J-M et al., Proc. Natl. Acad. Sci. USA (1976), 73 945, following activation of the pro-collagenase in the conditioned medium by treatment with trypsin. Collagenase activity was measured using $^{14}$C-acetylated collagen type I from rat tail tendons as the substrate and employing the microtitre plate assay method of Johnson-Wint, B, Anal. Biochem. (1980), 104, 175. The IC$_{50}$ is that concentration of a compound or salt of the invention in the enzyme digestion which reduces substrate cleavage and solubilization to 50% of that achieved by the enzyme alone.

The results obtained in the foregoing test with representative compounds and salts of the invention are compiled in Table I hereinafter:

| Compound of formula I | IC$_{50}$ (nM) |
|---|---|
| A | 10 |
| B | 6 |
| C | 5 |
| D | 15 |
| E | 7 |
| F | 1.2 |
| G | 6.9 |

Compound A: 4-[2(R)-[1(R or S)-(Hydroxycarbamoyl)-2-phthalimidoethyl]-4-methylvaleryl]morpholine.
Compound B: 4-[2(R)-(1(R or S)-(Hydroxycarbamoyl)-2-phthalimidoethyl]-4-methylvaleryl]tetrahydro-1,4-thiazine.
Compound C: 1-[2(R)-(1(R or S)-(Hydroxycarbamoyl)-2-phthalimidoethyl]-4-methylvaleryl]-4-piperidinol.
Compound D: 1-[2(R)-[1(R or S)-(Hydroxycarbamoyl)-2-(1,2-dimethyl-3,5-dioxo-1,2,4-triazolidin-4-yl)ethyl]-4-methylvaleryl]piperidine.
Compound E: 4-[2(R)-[1(R or S)-(Hydroxycarbamoyl)-2-(3-methyl-2,5-dioxo-1-imidazolidinyl)ethyl]-4-methylvaleryl]tetrahydro-1,4-thiazine.
Compound F: Hexahydro-2-[2(R)-[1(R or S)-(hydroxycarbamoyl)-2-phthalimidoethyl]-4-methylvaleryl]-N-methyl-3(S)-pyridazine-carboxamide.
Compound G: 1-[2(R)-[1(R or S)-(Hydroxycarbamoyl)-2-(3,4,4-trimethyl-2,5-dioxo-1-imidazolidinyl)ethyl]-4-methylvaleryl]-4-piperidinol The compounds of formula I and their pharmaceutically acceptable salts can be used as medicaments, for example, in the form of pharmaceutical preparations. The pharmaceutical preparations can be administered orally, for example, in the form of tablets, coated tablets, dragées, hard and soft gelatin capsules, solutions, emulsions or suspensions. However, they can also be administered rectally, for example, in the form of suppositories, or parenterally, for example, in the form of injection solutions.

For the preparation of pharmaceutical preparations, the compounds of formula I and their pharmaceutically acceptable salts can be formulated with therapeutically inert, inorganic or organic carriers. Lactose, corn starch or derivatives thereof, talc, stearic acid or its salts can be used, for example, as such carriers for tablets, coated tablets, dragées and hard gelatine capsules. Suitable carriers for soft gelatin capsules are, for example, vegetable oils, waxes, fats, semi-solid and liquid polyols and the like. Depending on the nature of the active ingredient, no carriers are, however, generally required in the case of soft gelatin capsules. Suitable carriers for the preparation of solutions and syrups are, for example, water, polyols, saccharose, invert sugar, glucose and the like. Suitable carriers for the preparation of injection solutions are, for example, water, alcohols, polyols, glycerine, vegetable oils and the like. Natural and hardened oils, waxes, fats, semi-liquid polyols and the like are suitable carriers for the preparation of suppositories.

The pharmaceutical preparations can also contain preservatives, stabilizers, wetting agents, emulsifiers, sweeteners, colorants, flavorants, salts for adjustment of the osmotic pressure buffers coating agents or antioxidants.

Medicaments containing a compound of formula I or a pharmaceutically acceptable salt thereof and a therapeutically acceptable carrier as well aS a process for the preparation of such medicaments are also objects of the invention. The process comprises mixing a compound of formula I or a pharmaceutically acceptable salt thereof with a therapeutically inert carrier material and bringing the mixture into a galenical form for administration.

As mentioned earlier, a compound of formula I or its pharmaceutically acceptable salt can be usecl in the control or prevention of illnesses, especially in the control or prevention of degenerative joint diseases or in the treatment of invasive tumors, atherosclerosis or multiple sclerosis. The dosage at which a compound of formula I or its pharmaceutically acceptable salt can vary within wide limits and will, of course, be adjusted to the individual requirements in each particular case. In general, in the case of administration to adults, a daily dosage of from about 5 rng to about 30 mg, preferably from about 10 mg to about 15 mg, should be appropriate, although the upper limit may be exceeded when this is found to be expedient. The daily dosage can be administered as a single dosage or in divided dosages.

The Examples which follow further illustrate the invention. In these Examples all temperatures are givers in degrees Celsius.

Example I

A solution of 0.15g of 1-[2(R))-[1(R ,or S)-carboxy-2-phthalimidoethyl]-4-methylvaleryl]pyrrolidine (diastereoisomer 1) in 3 ml of dry dimethylformamide was cooled to 0° C. while stirring under nitrogen and treated successively with 0.075 g of 1 -hydroxybenzotriazole, 0.12 g of O-(tert.butyldimethylsilyl)hydroxylamine, 0.075 ml of N-methylmorpholine and 0.094 g of 1-ethyl-3-(3-dimethylaminopropyl)carbodiimide hydrochloride. The mixture was allowed to warm to room temperature and was stirred overnight. The solvent was evaporated and the residue was treated with 5 ml of 5% aqueous sodium hydrogen carbonate solution. The product was extracted with three portions of ethyl acetate and the combined extracts were washed with 1.0 M hydrochloric acid and aqueous sodium chloride solution. After drying over anhydrous magnesium sulfate, the solvent was evaporated and the residue was triturated with a mixture of ether and hexane. The solid was filtered and dried to give 0.09 g of 1-[2(R)-[1 (R or S)-(hydroxycarbamoyl)-2-phthalimidoethyl]-4-methylvaleryl]pyrrolidine (diastereoisomer 1) in the form of a white powder: nmr (MeOD): 7.84-7.71 (m,4H); 3.78-3.70 (m.3H); 3.54-3.43 (m,1H); 3.23-3.15 (m,1H); 3.05-2.90 (m,3H); 2.06-1.86 (m,2H); 1.83-1.71 (m,2H), 1.58-1.49 (m,1H); 1.43-1.32 (m,1H); 1.23-1.14 (m,1H); 0.87 (d,3H,J=6); 0.81 (d,3H,J=6); MS 402 (M+H)+.

The starting material was prepared as follows:

(i) A solution of 0.41 g of an approximatsly 6:1 mixture of diastereoisomer 1 and diastereoisomer 2 of 2(R)-[1(R or S)-(tert.butoxycarbonyl)-2-phthalimidoethyl]-4-methylvaleric acid in 5 ml of dry dimethyl-formamide was cooled to 0° C. while stirring under nitrogen and treated successively with 0.16 g of 1-hydroxybenzotriazole, 0.1 g of pyrrolidine, 0.13 ml of N-methylmorpholine and 0.23 g of 1-ethyl-3-(3-dimethylamino-propyl)carbodiimide hydrochloride. The mixture was allowed to warm to room temperature and was stirred overnight. The solvent was evaporated and the residue was treated with 20 ml of 5% aqueous sodium hydrogen carbonate solution. The product was extracted with three portions of ethyl acetate and the combined extracts were washed with 5% citric acid and aqueous sodium chloride solution. After drying over anhydrous magnesium sulfate, the solvent was evaporated to give 0.5 g of a colorless gum which was purified by flash chromatography on silica gel using hexane/ethyl acetate (5:4) for the elution. After elution of the faster moving product (diastereoisomer 2), there was obtained 0.365g of 1-[2(R)-[1(R or S)-(tert.butoxycarbonyl)-2-phtyalimido-ethyl]-4-methylvaleryl]pyrrolidine (diastereoisomer 1) in the form of a colorless gum; nmr (MeOD): 7.88-7.79 (m,4H); 3.99-3.93 (m,1H); 3.78-3.66 (m,2H); 3.60-3.53 (m,1H); 3.39-3.30 (m,1H); 3.27-3.21 (m,1H); 3.19-3.13 (m,1H); 3.06-2.99 (m,1H); 2.10-1.96 (m,2H); 1.92-1.83 (m,2H); 1.76-1.6,8 (m,1H) 1.53-1.42 (m,1H), 1.33 (s,gH); 1.30-1.20 (m,1H); 0.95 (d,3H,J=6); 0.88 (d,3H,J=6).

(ii) A solution of 0.35 g of 1-[2(R)-[1(R or S)-(tert.butoxycarbonyl)-2-phthalimidoethyl]-4- methylvaleryl]pyrrolidine (diastereoisomer 1), in 10 ml of dichloromethane was treated with 3 ml of trifluoroacetic acid. The mixture was stirred at room temperature for 2 hours and 10 ml of toluene were added. The solvent was evaporated and the residue was re-evaporated for an additional three times with 20 ml portions of toluene. The residue was crystallized from ether to give 0.161 g of 1-[2(R)-[1(R or S)-carboxy-2-phthalimidoethyl]-4-methylvaleryl]- pyrrolidine (diastereoisomer 1) in the form of a white solid; nmr (MeOD): 7.86-7.75 (m,4H); 3.92 (dd,1H,J=11,6); 3.80 (dd,1H, J=11,6); 3.74-3.67 (m,1H); 3.55-3.46 (m,1H); 3.32-3.18 (m,2H); 3.13-2.99 (m,2H); 2.06-1.90 (m,2H); 1.87-1.77 (m,2H); 1.71-1.62 (m,1H): 1.52-1.40 (m,1H); 1.33-1.25 (m,1H); 0.92 (d,3H,J=6); 0.86 (d,3H,J=6); MS: 387 (M+H)+.

Example 2

In a manner analogous to that described in the first paragraph of Example 1, from 0.155g of 1-[2(R)-[1(R or S)-carboxy-2-phthalimidoethyl]-4-methylvaleryl]-piperidine (diastereoisomer 1), prepared in a manner analogous to that described in Example 1(i)–(ii), there was obtained 0.1 g of 1[2(R)-[1(R or S)-(hydroxycarbamoyl)-2-phthalimidoethyl]-4-methylvaleryl]piperidine (diastereoisomer 1) iin the form of a white powder; nmr (MeOD): 7.88-7.76 (m,4H); 3.89 (dd,1H,J=11,6); 3.86-3.77 (m,1H); 3.70-3.58 (m,3H); 3.37-3.2.4 (m,2H); 2.99-2.93 (m,1H); 1.78-1.53 (m,6H); 1.52-1.36(m,2H); 1.23-1.14 (m,1H); 0.93-0.85 (m,6H); MS: 416 (M+H)+.

Example 3

In a manner analogous to that described in the first paragraph of Example 1, from 0.283 g of 4-[2(R)-[1(R or S)-carboxy-2phthalimidoethyl]-4-methylvaleryl]morpholine (diastereoisomer 1), prepared in a manner analogous to that described in Example 1(i)–(ii), there was obtained 0.12 g of 4-[2-(R)-[1(R or S)-(hydroxycarbamoyl)- -2-phthalimidoethyl]-4methylvaleryl]morpholine (diastereoisomer 1) in the form of a white powder; nmr (MeOD): 7.87-7.76 (m,4H); 3.87 (dd,1H,J=11,6); 3.83-3.70 (m,3H); 3.68-3.60 (m,3H); 3.59-3.51 (m,2H); 3.47-3.39 (m,1H); 3.32-3.23 (m,1H); 2.99-2.92 (m,1H); 1.66-1.58 (m,1H); 1.47-1.36 (m,1H); 1.24-1.14 (m,1H); 0.91-0.84 (m,6H); MS: 418 (M+H)+.

Example 4

In a manner analogous to that described in the first paragraph of Example 1, from 0.16 g of 1-[2(R)-[1(R or S)-carboxy-2-phthalimidoethyl]-4-methylvaleryl]hexahydroazepine (diastereoisomer 1), prepared in a manner analogous to that described in Example 1(i)–(ii), there was obtained 0.13 g of 1-[2(R)-[1(R or S)-(hydroxycarbamoyl) -2-phthalimidoethyl]-4methylvaleryl]hexahydroazepine (diastereoisomer 1) in the form of a white powder; nmr (MeOD); 7.88-7.76 (rn,4H); 3.95 (dd,1H,J=11,6); 3.84-3.76 (m,1H); 3.70-3.54 (m,3H); 3.37-3.25 (m,2H); 2.97-2.89 (m,1H); 1.94-1.77 (m,2H); 1.75-1.53 (m,7H); 1.51-1.40 (m,1H); 1.27-1.19 (m,1H); 0.92 (d,3H,J=6); 0.88 (d,3H,J=6); MS: 430 (M+H)+.

Example 5

In a manner analogous to that described in the first paragraph of Example 1, from 0.28 g of 4-[2(R)-[1(R or S)-carboxy-2-phthalimidoethyl]-4-methylvaleryl]tetrahydro- 1,4thiazine (diastereoisomer 1), prepared in a manner analogous to that described in Example 1(i)–(ii), there was obtained 0.14 g of 4-[2(R)-[1 (R or S)-(hydroxycarbamoyl)-2-phthalimidoethyl]-4-methylvaleryl] tetrahydro-1,4-thiazine (diastereoisomer 1)in the form of a white solid; nmr (MeOD): 7.84-7.73 (m,4H); 4.09-4.01 (m,1H); 3.93-3.81 (m,3H); 3.63-3.53 (m,2H); 3.29-3.21 (m,1H); 2.95-2.87 (m,1H); 2.76-2.69 (m,1H); 2.67-2.59 (m,1H); 2.57-2.46 (m,2H); 1.63-1.55 (m,1H); 1.43-1.32 (m,1H); 1.20-1.12 (m,1H); 0.86 (d,3H,J=6); 0.83 (d,3H,J=6); MS: 434 (M+H)+.

Example 6

In a manner analogous to that described in the first paragraph of Example 1, from 0.36 g of 1-[2(R)-[1(R or S)-carboxy-2-phthalimidoethyl]-4-methylvaleryl]-4-piperidinol (diastereoisomer 1), prepared in a manner analogous to that described in Example 1(i)–(ii), there was obtained, after purification of the crude product by flash chromatography on silica gel using dichloromethane/methanol (16:1) for the elution, 0.053g of 1-[2(R)-[1(R or S)-(hydroxycarbamoyl)-2-phthalimido-ethyl]-4-methylvaleryl]-4-piperidinol (diastereoisomer 1) in the form of a white powder; nmr (MeOD): 7.88-7.76 (m,4H); 4.15-3.79 (m,4H); 3.67-2.84 (m,2H); 2.06-1.73 (m,2H); 1.70-1.14 (m,5H); 0.95-0.84 (m,6H); MS: 432 (M+H)+.

Example 7

In a manner analogous to that described in Example 1, from 0.557 g of 2(R)-[1(R or S)-carboxy-2-phthalimidoethyl]-N,N,4-trimethylvaleramide (diastereoisomer 1), prepared in a manner analogous to that described in Example 1(i)–(ii), there was obtained, after purification of the product by flash chromatography using 2% methanol in dichloromethane for the elution, 0.053 g of 2(R)-[1(R or S)-(hydroxycarbamoyl)-2-phthalimidoethyl]-N,N,4-trimethylvaleramide in the form of a white solid; nmr (MOOD): 7.85-7.75 (m,4H); 3.84 (dd,J=14,7,1H); 3.68 (dd,J=14,10,1H); 3.18 (s,3H); 2.98-2.93 (m,1H); 2.75 (s,3H); 1.6-1.53 (m,1H); 1.4-1.3 (m,1H); 1.23-1.14 (m,1H); 0.88 (d,J=8,3H); 0.84 (d,J=8,3H). MS: 376 (M+H)+.

Example 8

In a manner analogous to that described in the first paragraph of Example 1, from 0.59 g of an approximately 6:1 mixture of diastereoisomer 1 and diastereoisomer 2 of $N^2$-[2(R)-[1(R or S)-carboxy-2-phthalimidoethyl]-4-rnethylvaleryl]-$N^1$-methyl-L-prolinamide, prepared in a manner analogous to that described in Example 1(i)–(ii), there was obtained, after crystallization of the product from a mixture of dichloromethane and ether, 0.12 g of diastereoisomer 1 of $N^2$-[2(R)-[1(R or S)-(hydroxycarbamoyl)-2-phthalimidoethyl]-4-methylvaleryl]-$N^1$ -methyl-L-proplinamide in the form of a white solid; nmr (MeOD); 7.86-7.75 (m,4H); 4.12-4.07 (m,1H); 3.92-3.83 (m,2H); 3.74-3.64 (m,2H); 3.13-3.04

(m,1H); 2.93-2.86 (m,1H); ; 267 (s,3H); 2.19-1.96 (m,3H); 1.91-1.82 (m,1H); 1.75-1.65 (m,1H); 1.64-1.55 (m,1H); 1.23-1.14 (m,1H); 0.93 (d,3H,J=6); 0.86 (d,3H,J=6); MS: 458 (M)+.

Example 9

In a manner analogous to that described in the first paragraph of Example 1, except that the reaction was only allowed to proceed for 3 hours, from 0.31 g of 1-[2(R)-[1(R or S)-carboxy-2-phthalimidoethyl]-4-methyvaleryl]-2(S)-pyrrolidinemethanol (diastereoisomer 1), there was obtained, after purification of the product by flash chromatography using dichloromethane/methanol (12:1) for the elution and crystallization from a mixture of ethyl acetate and ,ether, 0.06 g of 1-[2(R)-[1(R or S)-(hydroxycarbamoyl)-2-phthalimidoethyl ]-4methylvaleryl]-2(S)-pyrrolidinemethanol (diastereoisomer 1)in the form of a white solid; nmr (MeOD): 7.88-7.77 (m,4H); 3.863.73 (m,4H); 3.63-3.50 (m,2H); 3.98-3.27 (m,1H); 3.10-2.92 (m,2H); 2.07-1.83 (m,4H); 1.62-1.43 (m,2H); 1.28-1.17 (m,1H); 0.97-0.83 (m,6H); MS: 432 (M+H)+.

The starting material was prepared as follows:

A solution of 0.355 g of 1-[2(R)-[1(R or S)-(tert.butoxcarbonyl)-2-phthalimidoethyl]-4-methyl-valeryl]-2(S)-pyrrolidinemethanol (diastereoisomer 1), prepared in a manner analogous to that described in Example 1(i), in 7 ml of toluene was treated with 0.07 g of 3-methyl-3-pentenol and 0.7 ml of trimethylsilyl bromide. The mixture was stirred under a dry nitrogen atmosphere for 1.5 hours and then the solvent was evaporated. After three additional evaporations from 10 ml of toluene each time, there was obtained 0.31 g of a pale brown foam containing 1-[2(R)-[1(R or S)-carboxy-2-phthalimidoethyl]-4-methylvaleryl]-2(S)-pyrrolidinemethanol (diastereoisomer 1 ) which was used without further purification.

Example 10

In a manner analogous to that described in the first paragraph of Example 1, from 0.568 g of an approximately 6:1 mixture of diastereoisomer 1 and diastereoisomer 2 of 1-[2(R)-[1(R or S)-carboxy-2-phthalimidoethyl]-4-rnethylvaleryi]-4methylpiperazine hydrobromide, prepared in a manner analogous to that described in Example 9(i), there was obtained, after purification of the product by flash chromatography on silica gel using dichloromethane/methanol ( 12:1 ) for the elution and precipitation of the hydrochloride by the adclition of hydrogen chloride in ethyl acetate, 0.105g of 1-[2(R)-1(R or S)-(hydroxycarbamoyl)-2-phthalimidoethyl]-4-methylvaleryl]-4methylpiperazine hydrochloride (diastereoisomer 1)in the form of a white solid; nmr (MeOD): 7.89-7.79 (m,4.H); 4.18-3.80 (m,4H); 3.74 (dd,1H,J=11,5); 3.48-3.18 (br m,6H); 2.93-2.84 (m,4H); 1.76-167 (m,1H); 1.52-1.42 (m,1H), 1.35-1.27 (m,1H); 0.93 (d,3H,J=6); 0.89 (d,3H,J=5.5); MS: 431 (M+H)+.

Example 11

In a manner analogous to that described in the first paragraph of Example 1, from 0.29 g of 4-[2(R)-[1(R or S)-carboxy-2-phthalimidoethyl ]-4-methylvaleryl]tetrahydro-1,4-thiazine 1,1-dioxide (diastereoisomer 1), there was obtained 0.13g of 4-[2(R)-[1(R or S)-(hydroxycarbamoyi)-2-phthalimidoethyl]-4-methylvaleryl]tetrahydro-1,4-thiazine 1,1 -dioxide (diastereoisomer 1)in the form of a white solid; nmr (MeOD): 7.88-7.75 (m,4H); 4.33-4.23 (m,1H); 4.20-4.04 (m,2H); 3.93 (dd,1H,J=11,6); 3.87-3.78 (m,1H); 3.73 (dd,1H,J=11,5); 3.443.28 (m,3H); 3.22-3.03 (m,3H); 2.97-2.90 (m,1H); 1.67-1.57 (m,1H); 1.51-1.38 (m,1H); 1.34-1.25 (m,1H); 0.93-0.84 (m,6H); MS: 466 (M+H)+.

The starting material was prepared as follows:

(i) A solution of 0.3 g of 4-[2(R)-[1(R or S)-(tert.butoxycarbonyl)-2-phthalimidoethyl]-4-methylvaleryl]tetrahydro-1,4-thiazine (diastereoisomer 1) in 20 ml of dichloromethane was cooled to 0° C. and treated with 0.3 g of 85% m-chloroperoxybenzoic acid. The mixture was stirred at ambient temperature overnight and then the solution was washed twice with 5% aqueous sodium hydrogen carbonate solution, dried over anhydrous magnesium sulfate and evaporated to give a white foam. After purification by flash chromatography on silica gel using ethyl acetate/hexane (2:3) for the elution, there was obtained 0.33 g of 4-[2(R)-[1(R or S)-(tert.butoxycarbonyl)-2-phthalimidoethyl]-4-methylvaleryl]-tetrahydro-1,4-thiazine 1,1-dioxide (diastereoisomer 1) in the form of a white foam which solidified to a white solid; nmr (MeOD); 7.89-7.78 (m,4H); 4.36-4.23 (m,2H); 4.11 (dd,1H,J=11,7); 4.07-3.98 (m,1H); 3.85-3.73 (m,2H); 3.44-3.113 (m,2H); 3.21-3.05 (m,4H); 1.73-1.64 (m,1H); 1.61-1.59 (m,1H); 1.40-1.32 (m,1H); 1.28 (s,9H); 0.95-0.88 (m,4H).

(ii) In a manner analogous to that described in Example 1(ii), from 0.33g of 4-[2(R)-[1(R or S)-(tert.butoxycarbonyl)-2-phthalimidoethyl]-4-methylvaleryl]tetrahydro-1,4-thiazine 1,1 -dioxide (diastereoisomer 1) there was obtained 0.29 g of 4-[2(R)-[1 (R or S)-carboxy-2-phthalimidoethyl]-4-methylvaleryl]tetrahydro-1,4-thiazine 1,1 -dioxide (diastereoisomer 1) in the form of a white foam which was used without further purification.

Example 12

In a manner analogous to that described in the first paragraph of Example 1, from 0.3 g of 8-[2(R)-[1(R or S)-carboxy-2-phthalimidoethyl]-4-methylvaleryl]-1,4-dioxa-8-azaspiro[4.5]decane (diastereoisomer 1) prepared in a manner analogous to that described in Example 1(i)–(ii), there was obtained, after purification of the product by flash chromatography on silica gel using ethyl acetate/methanol (200:5) for the elution, 0.105g of 8-[2(R)-[1(R or S)-(hydroxycarbamoyl)-2-phthalimidoethyl]-4-methylvaleryl]- 1,4-dioxa-8-azaspiro[4.5]decane (diastereoisomer 1) in the form of a white solid; nmr (MeOD): 7.87-7.75. (m,4H); 3.97 (m,4H); 3.91-3.81 (m,2H) 3.79-3,60 (m,3H); 3.45-3.26 (m,2H); .3.00-2.91 (m,1H); 1.89-1.80 (m,1H); 1.74-1.51 (m,4H); 1.45-1.31 (m,1H); 1.23-1.13 (m,1H); 0.88 (d,3H,J=6); 0.85 (d,3H,J=5.5); MS: 474 (M+H)+.

Example 13

A solution of 0.13g of 1-[2(R)-[1(R or S)-(benzyloxcarbamoyl)-2-(1,2-dimethyl -3,5-dioxo- 1,2,4-triazolidin-4-yl) ethyl]-4-methylvaleryl]piperidine (diastereoisomer 1) in 7.0 ml of methanol was hydrogenated in the presence of 40 mg of 10% palladium-on-charcoal for 30 minutes. The catalyst was removed by filtration and the solution was evaporated to give 0.076 g of 1-[2(R)-[1(R or S)-(hydroxycarbamoyl)-2-( 1,2-dimethyl-3,5-dioxo-1,2,4-triazolidin-4-yl) ethyl]-4-methylvaleryl]piperidine (diastereoisomer 1) in the form of a white solid; nmr (MeOD): 3.81-3.72 (m,2H); 3.67 (dd,1H,J=11,7); 3.64-3.55 (m,1H); 3.44 (dd,1H,J=11,5); 3.39-3.23 (m,2H); 3.11 (s,6H); 2.96-2.88 (m,1H); 1.77-1.33 (m,8H); 1.19-1.11 (m,1H); 0.87 (d,3H,J=6); 0.85 (d,3H,J=6); MS: 398 (M+H)+.

The starting material was prepared as follows:

(i) 0.284 g of 60% sodium hydride was added to a stirred ice-cold solution of 3.01 g of 1,2-dibenzyl 1-tert.butyl 4-methyl-1,1,2(R)-pentanetricarboxylate in 50 ml of dry dimethylformamide under a nitrogen atmosphere. The mixture was stirred for 30 minutes at 0° and for an additional 1.5 hours at ambient temperature, and again cooled to 0° before the addition of 1.6 g of 4-bromomethyl-1,2-dimethylurazole. The mixture was allowed to return to ambient temperature and was stirred for 3 hours. The volatiles were evaporated under high vacuum and the residue was dissolved in ethyl acetate and washed with 5% aqueous citric acid solution, water and saturated sodium chloride solution. After drying over anhydrous magnesium sulfate, the solvent was evaporated and the residue was purified by flash chromatography on silica gel using hexane/ether (1:1) followed by ether for the elution. There were obtained 2.464 g of 1,2-dibenzyl 1 -tert.butyl 4-methyl-l-[(1,2-dimethyl-3,5-dioxo-1,2,4-triazolidin-4-yl) methyl]-1,1,2(R)-pentanetricarboxylate in the form of a colorless oil.

(ii) 2.464 g of 1,2-dibenzyl 1 -tert.butyl 4-methyl-1 -[(1,2-dimethyl-3,5-dioxo- 1,2,4-triazolidin-4-yl)methyl]-1,1,2(R)-pentanetricarboxylate were dissolved in 40 ml of methanol containing 0.25 g of 10% palladium-on-charcoal catalyst. The mixture was hydrogenated for 2 hours, the catalyst was removed by filtration and the solvent evaporated to give 1-(tert.butoxycarbonyl)-4-methyl-1-[(1,2-dimethyl-3,5-dioxo-1,2,4-triazolidin-4-yl) methyl]-1,2(R)-pentanedicarboxyic acid in the form of a colorless gum. The gum was dissolved in 60 ml of toluene containing 0.43 ml of N-methylmorpholine and the mixture was heated under reflux for 1 hour. The solution was washed with 5% aqueous citric acid solution, water and saturated aqueous sodium chloride, dried over anhydrous magnesium sulfate and evaporated to give 1.422 g of 2(R)-[1(R or S)-(tert.butoxycarbonyl)-2-( 1,2-dimethyl-3,5-dioxo-1,2,4-triazolidin-4-yl) ethyl]-4-methylvaleric acid in the form of a waxy solid as an approximately 6:1 mixture of diastereoisomer 1 and diastereoisomer 2.

(iii) In a manner analogous to that described in Example(i) from 0.831 g of an approximately 6:1 mixture of diastereoisomer 1 and diastereoisomer 2 of 2(R)-[I(R or S)-(tert.butoxycarbonyl)]-2-(1,2-dimethyl-3,5-dioxo- 1,2,4-triazolidin-4-yl)ethyl]-4-methylvaleric acid, there was obtained 0.462 g of 1-[2(R)-[1(R or S )-(tert.butoxycarbonyl)-2-(1,2-dimethyl-3,5-dioxo- 1,2,4-triazolidin-4-yl) ethyl]-4-methylvaleryl]piperidine (diastereoisomer 1) in the form of a colorless oil.

(iv) A solution of 0.462g of 1-[2(R)-[1(R or S)-(tert.butoxycarbonyl)-2-( 1,2-dimethyl-3,5-dioxo-1,2,4-triazolidin-4-yl) ethyl]-4-methylvaleryl]piperidine (diastereoisomer 1) in 7 ml of dichloromethane was treated with 0.85 ml of trifluoroacetic acid. The mixture was stirred at room temperature for 1.5 hours and then toluene was added and the solvents were evaporated. After an additional three evaporations from toluene, the residue was dissolved in 11 ml of dry dimethylformamide, cooled to 0° and stirred under nitrogen during successive additions of 0.13 g of O-benzylhydroxylamine, 0.152 g of 1-hydroxybenzotriazole, 0.25 ml of N-methylmorpholine and 0.208 g of 1-ethyl-3.-(3-dimethylaminopropyl)-carbodiimide hydrochloride. The mixture was allowed to warm to room temperature and was stirred overnight. The solvent was evaporated and tile residue was treated with 5% aqueous sodium hydrogen carbonate solution. The product was extracted with ethyl acetate and the ethyl acetate extract was washed with 5% citric acid solution and aqueous sodium chloride solution. After drying over anhydrous magnesium sulfate, the solvent was evaporated and the residue was purified by flash chromatography on silica gel using ethyl acetate for the elution. In addition to 0.14 g of recovered starting material, there was obtained 0.142 g of 1-[2(R)-[1(R or S)-(benzyloxy-carbamoyl) - 2-( 1,2-dimethyl- 3,5-dioxo-1,2,4-triazolidin-4-yl)ethyl]-4-methylvaleryl]piperidine (diastereoisomer 1)in the form of white solid; nmr (CDCl3): 9.77 (s,1H); 7.44-7.29 (m,5H); 4.90 (q,2H, J=8); 3.78 (dd,1H,J=11,5); 3.70-3.63 (m,2H); 3.62-3.53 (m,1H); 3.49-3.42 (m,1H); 3.41-3.33 (m,1H); 3.28-3.22 (m,1H); 3.10 (s,6H); 3.00-2.93 (m,1H); 1.81-1.38 (m,8H); 1.29-1.23 (m,1H); 0.88 (d,3H,J=6); 0.85 (d,3H,J=6).

Example 14

In a manner analogous to that described in the first paragraph of Example 13, from 0.182 g of 1-[2(R)-[1(R or S)-(benzyloxycarbamoyl)-2-(2,6-dioxopiperidino)ethyl]-4-methylvaleryl]piperidine (diastereoisomer 1), there was obtained 0.066g of 1-[2(R)-[1(R or S)-(hydroxycarbamoyl)-2-(2,6-dioxopiperidino) ethyl]-4-methylvaleryl]piperidine (diastereoisomer 1)in the form of a white solid; nmr (MeOD): 4.06 (dd,1H,J=11,6.5); 3.80-3.57 (m,4H); 3.53-3.46 (m,1H); 3.34-3.24 (m,1H)); 2.68-2.54 (m,5H); 1.92-1.82 (m,2H); 1.76-1.45 (m,7H); 1.44-1.32 (m,1H); !.14-1.06 (m,1H); 0.87 (d,3H,J=6); 0.83 (d,3H,J=6); MS: 382 (M+H)+.

The starting material was prepared as follows:

(i) In a manner analogous to that described in Example 13(i)–(iii), from 1,2-dibenzyl 1-tert.butyl 4-methyl-1,1,2(R)-pentanetricarboxylate and N-bromomethylglutarimide, there was obtained 1-[2(R)-[1(R or S)-(tert.butoxycarbonyl)-2-(2,6-dioxopiperidine) ethyl]-4-methylvaleryl]piperidine (diastereoisomer 1) in the form of a colorless gum.

(ii) A solution of 0.324 g of 1-[2(R)-[1(R or S)-(tert.butoxycarbonyl)-2-(2,6-dioxopiperidino)ethyl]-4-methylvaleryl]piperidine (diastereoisomer 1) in 6.5 ml of toluene was treated with 0.065 g of 3-methyl-3-pentanol and 0.65 ml of trimethylsilyl bromide. The mixture was stirred under a dry nitrogen atmosphere for 1 hour and then the solvent was evaporated. After three additional evaporations from toluene, the residue was dissolved in 10 ml of dry dimethylformamide, cooled to 0° and stirred under nitrogen during successive additions of 0.095 g of O-benzylhydroxyl-amine, 0.111 g of 1-hydroxybenzotriazole 0.18 ml of N-methylmorpholine and 0.152 g of 1-ethyl-3-(3-dimethylaminopropyl)carbodiimide hydro-chloride. The mixture was allowed to warm to room temperature and was stirred overnight. The solvent was evaporated and the residue was treated with 5% aqueous sodium hydrogen carbonate solution. The product wats extracted with ethyl acetate and the ethyl acetate extract weis washed with 5% citric acid solution and aqueous sodium chloride solution. After drying over anhydrous magnesium sulfate, the solvent was evaporated and the residue was purified by flash chromatography on silica gel using hexane/ethyl acetate (7:2) for the elution. There was obtained 0.182 g of 1-[2(R)-[1(R or S)-(benzyloxycarbamoyl)-2-(2,6-dioxo-piperidino)ethyl]-4-methylvaleryl]piperidine (diastereoisomer 1) in the form of a white solid; nmr (CDCl$_3$): 9.23 (s,1H); 7.46-7.31 (m,5H); 4.96-4.88 (m,2H): 3.98 (dd,1H,J=11,5); 3.89-3.76 (m,2H); 3.74-3.64 (m,1H); 3.52-3.42 (m,1H); 3.33-3.21 (m,2H); 2.76-2.67 (m,1H); 2.63-2.52 (m,4H); 1.94-1.37 (m,10H); 1.24-1.14 (m,1H); 0.88 (d,3H,J=6); 0.84 (d,3H,J=6).

Example 15

In a manner analogous to that described in the first paragraph of Example 13, from 0.39 g of 1-[2(R)-[1(R or S)-(benzyloxycarbamoyl)-2-(3,4,4-trimethyl-2,5-dioxo-1-imidazolidinyl)ethyl]-4-methylvaleryl]piperidine (diastereoisomer 1), there was obtained 0.255g of 1-[2(R)-[1(R or S)-(hydroxycarbamoyl)-2-(3,4,4-trimethyl-2,5-dioxo-1-imidazolidinyl)ethyl]-4-methylvaleryl]piperidine (diastereoisomer 1) in the form of a white solid; nmr (MeOD): 3.84-3.63 (m,4H); 3.49-3.41 (m,1H); 3.38-3.25 (m,2H); 2.90-2.83 (m,4H); 1.80-1.28 (m,14H); 1.19-1.11 (m,1H); 0.89 (d,3H,J=5.5); 0.86 (d,3H,J=5.5); MS: 411 (M+H)+.

The starting material was prepared as follows:

In a manner analogous to that described in Example 14(i)–(ii), from 1,2-dibenzyl 1-tert.butyl 4-methyl-1,1,2(R)-pentanetricarboxylate and 3-bromomethyl-1,5,5-trimethylhydantoin, there was obtained 1-[2(R)-[1(R or S)-(benzyloxycarbamoyl)-2-(3,4,4-trimethyl-2,5-dioxo-1-imidazolidinyl)ethyl]-4-methylvaleryl]piperidine (diastereoisomer 1) in the form of a white foam; nmr (CDCl$_3$): 9.50 (brs,1H); 7.45-7.39 (m,5H); 3.79-3.56 (m,4H); 3.52-3.42 (m,1H) 3.33-3.23 (m,2H); 2.94-2.80 (m,4H); 1.93-1.29 (m,14H); 1.26-1.16 (m,1H); 0.87 (d,3H,J=6); 0.84 (d,3H,J=6).

Example 16

In a manner analogous to that described in the first paragraph of Example 13, from 0.335 g of 4-[2(R)-[1(R or S)-(benzyloxycarbamoyl)-2-(3-methyl-2,5-dioxo-1-imidazolidinyl)-ethyl]-4-methylvaleryl]morpholine (diastereoisomer 1), there was obtained 0.198g of 4-[2(R)-[1(R or S)-(hydroxycarbamoyl)-2-(3-methyl-2,5-dioxo-1-imidazolidinyl)ethyl]-4methylvaleryl]morpholine (diastereoisomer 1) in the form of a white solid; nmr (MeOD): 3.78 (s,2H); 3.73-3.45 (m,9H); 3.36 (dd, 1H, J=11,5); 3.18-3.10 (m,1H); 2.85 (s,3H); 2.82-2.75 (m,1H); 1.57-1.47 (m,1H); 1.38-1.26 (m,1H) 1.14-1.05 (m,1H); 0.82-0.75 (m,6H); MS: 385 (M+H)+.

The starting material was prepared as follows:

In a manner analogous to that described in Example 15(i)–(ii), from 1,2-dibenzyl 1-tert.butyl 4-methyl-1,1,2(R)-pentanetricarboxylate and 3-bromomethyl-l-methylhydantoin, there was obtained 4-[2(R)-[1(R or S)-(benzyloxycarbamoyl)-2-(3-methyl-2,5-dioxo-1-imidazolid nyl)ethy11]-4methylvaleryl]morpholine (diastereoisomer 1) in the form of a white solid; MS: 475 (M+H)+.

Example 17

In a manner analogous to that described in the first paragraph of Example 1, from 0.273 g of 1-[2(R)-[1(R or S)-carboxy-2-(3-methyl-2,5-dioxo-1-imidazolidinyl)ethyl]-4-methylvaleryl]piperidine (diastereoisomer 1), there was obtained 0.023g of 1-[2(R)-[1(R or S)-(hydroxycarbamoyl)-2-(3-methyl-2,5-dioxo-1-imidazolidinyl)ethyl]-4-methylvaleryl]piperidine (diastereoisomer 1) in the form, of a white solid; nmr (MeOD); 3.78 (s,2H); 3.74-3.64 (m,2H); 3.63-3.48 (m,2H); :3.35-3.26 (m,2H); 3.25-3.15 (m,1H); 2.85 (s,3H); 2.82-2.73 (m,1H); 1.68-1.25 (m,8H); 1.10-1.03 (m,1H); 0.82 (d,3H,J=6); 0.75 (d,3H,J=6); MS: 383 (M+H)+.

The starting material was prepared as follows:

In a manner analogous to that described in Example 1(ii), from 0.325g of 1-[2(R)-[1(R or S)-(tert.butoxycarbonyl)-2-(3-methyl-2,6-dioxo-1-imidazolidinyl)ethyl]-4-methylvaleryl]piperidine (diastereoisomer 1), prepared in a manner analogous to that described in Example 13(i)–(iii) from 1,2-dibenzyl 1-tert.butyl 4-methyl-1,1,2(R)-pentanetricarboxylate and 3-bromomethyl-1-methylhydantoin, there was obtained 0.273 g of 1-[2(R)-[1(R or S)-carboxy-2-(3-methyl-2,5-dioxo-1-imidazolidinyl)ethyl]-4-methylvaleryl]piperidine (diastereoisomer 1) in the form of a colorless gum which was used without further purification.

Example 18

In a manner analogous to that described in the first paragraph of Example 1, from 0.45 g of 4-[2(R)-[1(R or S)-carboxy-2-(3-methyl-2,5-dioxo-1-imidazolidinyl)ethyl]-4-methylvaleryl]tetrahydro-1,4-thiazine (diastereoisomer 1) there was obtained 0.155 mg of 4-[2(R)-[1(R or S)-(hydroxycarbamoyl)-2-(3-methyl-2,5-dioxo-1-imidazolidinyl)ethyl]-4-methylvaleryl]tetrahydro-1,4-thiazine (diastereoisomer 1) in the form of a white solid; nmr (MeOD): 4.09-3.88 (m,3H); 3.86 (s,2H); 3.78-3.70 (m,1H); 3.66 (dd,1H,J=11,7); 3.42 (d.d, 1H, J=11,5); 3.29-3.21 (m,1H); 2.92 (s,3H); 2.88-2.82 (m,1H); 2.78-2.71 (m,1H); 2.68-2.54 (m,3H); 1.65-1.57 (m,1H); 1.46-1.34 (m,1H); 1.22-1.15; (m,1H); 0.90-0.84 (m,6H); MS: 401 (M+H)+.

The starting material was prepared as follows:

(i) In a manner analogous to that described in Example 13(i)–(iii), from 1,2-dibenzyl 1-tert.butyl 4-methyl-1,1,2(R)-pentanetricarboxylate and 3-bromomethyl-1-methylhydantoin, there was obtained 4-[2(R)-[1-(R or S)-(terl.butoxycarbonyl)-2-(3-methyl-2,5-dioxo-1-imidazolidinyl)ethyl]-4methylvaleryl]tetrahydro-1,4-thiazine (diastereoisomer 1) in the form of a white solid; nmr (MeOD): 3.98-3.84 (m,6H); 3.77 (dd,1H,J=11,7); 3.47 (dd,1H, J=11,5); 3.22-3.14 (m,1H); 3.09-3.03 (m,1H); 2.95 (s,3H); 2.81-2.73 (m,1H); 2.69-2.55 (m,3H); 1.77-1.68 (m,1H); 1.53-1.39 (m,10H); 1.26-1.18 (m,1H); 0.94-0.86 (m,6H).

(ii) A solution of 0.52g of 4-[2(R)-[1(R or S)-(tert.butoxycarbonyl)-2-(3-methyl-2,5-dioxo-1-imidazolidinyl)ethyl]-4-methylvaleryl]tetrahydro-1,4-thiazine (diastereoisomer 1) in 15 ml of dichloromethane was treated with 1.05 ml of 4M hydrogen chloride in dioxane. The solution was stirred at room temperature for 3.25 hours and then 25 ml of toluene was added and the solvents were evaporated. After three additional evaporations from 25 ml of toluene, there was obtained 0.45g of 4-[2(R)-[1(R or S)-carboxy-2-(3-methyl-2,5-imidazolidinyl)

ethyl]-4-methylvaleryl]tetrahydro-1,4-thiazine (diastereoisomer 1) in the form of a colorless gum that was used directly without further purification.

Example 19

In a manner analogous to that described in the first paragraph of Example 13, from 0.278g of 4-[2(R)-[1(R or S)-(benzyloxycarbamoyl)- 2-( 2,5-dioxo-1-pyrrolidinyl)ethyl]-4-methylvaleryl]morpholine (diastereoisomer 1), there was obtained 0.151 g of 4-[2(R)-[1(R or S)-(hydroxycarbamoyl)-2-(2,5-dioxo-1-pyrrolidinyl) ethyl]-4-methylvaleryl]morpholine (diastereoisomer 1) in the form of a white solid; nmr (MeOD); 3.73-3.49 (m,9H); 3.34 (dd,1H,J=11,5); 3.19-3;.11 (m,1H); 2.74-2.66 (m,1H); 2.55 (s,4H); 1.57-1.49 (m,1H), 1.38-1.26 (m,1H); 1.12-1.03 (m,1H); 0.82-0.75 (m,6H); MS: 370 (M+H)+.

The starting material was prepared as follows:

In a manner analogous to that described in Example 14(i)-(ii), from 1,2-dibenzyl 1-tert.butyl 4-methyl-1,1,2(R)-pentane-tricarboxylate and N-bromomethylsuccinimide, there was obtained 4-[2(R)-[1(R or S)-(benzyloxycarbamoyl)-2-(2,5-dioxo-1-pyrrolidinyl) ethyl]-4-methylvaleryl]morpholine (diastereoisomer 1) in the form of a white solid; MS: 460 (M+H)+.

Example 20

In a manner analogous to that described in the first paragraph of Example 13, from 0.19 g of 4-[2(R)-[1(S or R)-(benzylcarbamoyl)- 2-( 2-oxo-1-pyrrolidinyl)ethyl]-4-methylvaleryl]morpholine (diastereoisomer 1), there was obtained 0.104 g of 4-[2(R)-[1(R or S)-(hydroxycarbamoyl)-2-(2-oxo-1-pyrrolidinyl) ethyl]-4-methylvaleryl]morpholine (diastereoisomer 1) in the form of a white solid; nmr (MeOD): 3.70-3.39 (m,8H); 3.36-3.17 (m,4H); 3.14-3.05 (m,1H); 2.57-2.48 (m,1H); 2.28-2.17 (m,2H); 1.96-1.84 (m,2H); 1.62-1.52 (m,1H); 1.58-1.24 (m,1H); 1.13-1.03 (m,1H); 0.83-0.75 (m,6H); MS: 356 (M+H)+.

The starting material was prepared as follows:

In a manner analogous to that described in Example 14(i)-(ii), from 1,2-dibenzyl 1-tert.butyl 4-methyl-1,1,2(R)-pentanetricarboxylate and N-bromomethylpyrrolidine, there was obtained 4-[2(R)-[1(R or S)-(benzyloxycarbamoyl)-2-(2-oxo-1-pyrrolidinyl)ethyl]-4-methylvaleryl]morpholine (diastereoisomer 1) in the form of a white solid; MS: 446 (M+H)+.

Example 21

In a manner analogous to that described in the first paragraph of Example 13, from 0.335 g of 1-[2(R)-1(R or S)-(benzyloxycarbamoyl)-2-( 2-oxo-1-pyrrolidinyl)ethyl]-4methylvaleryl]piperidine (diastereoisomer 1), there was obtained 0.19g of 1-[2(R)-[1(R or S)-(hydroxycarbamoyl)-2-(2-oxo-1-pyrrolidinyl)ethyl]-4-methylvaleryl]piperidine (diastereoisomer 1) in the form of a white solid; nmr (MeOD): 3.78-3.58 (m,3H); 3.53-3.33 (m,4H); 3.27-3.17 (m,2H); 2.63-2.54. (m,1H); 2.34-2.26 (m,2H); 2.03-1.93 (m,2H); 1.77-1.45 (m,7H); 1.43-1.30 (m,1H); 1.20-1.08 (m,1H); 0.93-0.83 (m,6H); MS: 354 (M+H)+.

The starting material was prepared as follows:

In a manner analogous to that described in Example 14(i)-ii), from 1,2-benzyl 1-tert.butyl 4-methyl-1,1,2(R)-pentanetricarboxylate and N-bromomethylpyrrolidine, there was obtained 1-[2(R)-[1(R or S)-(benzyloxycarbamoyl)-2-(2-oxo-1-pyrrolidinyl)ethyl]-4-methyl-valeryl]piperidine (diastereoisomer 1) in the form of a white solid; MS: 444 (M+H)+.

Example 22

In a manner analogous to that described in the first paragraph of Example 1, from 0.226 g of 4-[2(R)-[1(R or S)-carboxy-3-phthalimidopropyl]-4-methylvaleryl]morpholine there was obtained 0.065 g of 4-[2(R)-[1(R or S)-(hydroxycarbamoyl)- 3-phthalimidopropyl]-4-methylvaleryl]morpholine (diastereoisomer 1) in the form of a white solid; nmr (MeOD): 7.88-7.76 (m,4H); 3.86-3.50 (m,8H); 3.24-3.15 (m,1H); 2.32-2.23 (m,1H) ;1.99-1.89 (m,1H); 1.83-1.73 (m,1H); 1.66-1.57 (m,1H); 1.43-1.29 (m,1H); 1.17-1.09 (m,1H); 0.89-0.83 (m,6H); MS: 432 (M+H)+.

The starting material was prepared as follows:

In a manner analogous to that described in Example 1(i)-(ii), from 0.65 g of an approximately 5:1 mixture, of diastereoisomers of 2(R)-[1(R or S)-(tert.butoxycarbonyl)-3-phthalimidopropyl]-4-methylvaleric acid and 0.17 ml of morpholine, there was obtained 0.462g of 4-[2(R)-[1(R or S)-carboxy-3-phthalimidopropyl]-4-methylvaleryl]morpholine in the form of a colorless gum which was used without further purification.

Example 23

In a manner analogous to that described in Example 13, from 0.2g of N,N-diethyl-2(R)-[l(R or S)-(benzyloxycarbamoyl)-2-phthalimidoethyl]-4-methylvaleramide (diastereoisomer 1 ), prepared in a manner analogous to that described in Example 13(iii)-(iv), there was obtained, after purification of the product by flash chromatography using 3% methanol in dichloromethane for the elution, 0.085 g of N,N-diethyl-2(R)-[1(R or S)-(hydroxycarbamoyl)-2-phthalimidoethyl]-4-methylvaleramide (diastereoisomer 1) in the form of a white solid; nmr (MeOD): 7.85-7.75 (m,4H); 3.97 (dd,J=14,10,1H); 3.68-3.6 (m,1H); 3.57-3.48 (m,2H); 3.38 (q,J=7,2H); 3.2 (dt,J=12,4,1H); 2.84 (dt,J=14,5, 1H); 1.67-1.59 (m,1H); 1.47-1.36 (m,lH); 1.26 (t,J=8,3H); 1.25-1.16 (m,1H); 1.13 (t,J=8,3H); 0.9 (d,J=6,3H); 0.85 (d,J=6,3H). MS: 404 (M+H)+.

Example 24

In a manner analogous to that described in Example 1, from 0.16g of 3-[2(R)-[1(R or S)-carboxy-2-phthalimidoethyl]-4-methylvaleryl]thiazolidine (diastereoisomer 1), prepared in a manner analogous to that described in Example 1(i)-(ii), there was obtained, after purification of the product by flash chromatography using 5% methanol in dichloromethane for the elution, 0.039g of 3-[2(R)-[1(R or S)-(hydroxycarbamoyl)-2-phthalimidoethyl]-4-methylvaleryl]thiazolidine (diastereoisomer 1) in the form of a white solid; nmr (MeOD): 7.86-7.75 (m,4H); 4.8 (d,J=10,0.5H); 4.63 (d,J=10,0.5H); 4.36 (d,J=10,0.5H); 4.13-4.07 (m,0.5H); 4.03 (d,J,=10,0.5H); 3.87-3.72 (m,2H); 3.63-3.55 (m,0.5H); 3.45-3.36 (m,0.5H); 3.24-2.95 (m,2.5H); 1.62-1.54 (m,1H); 1.46-1.37 (m,1H); 1.29-1.2 (m,1H); 0.9 (d,J=6,3H); 0.85 (d,J=6,3H). MS: 420 (M+H)+.

Example 25

In a manner analogous to that described in Example 13, from 0.25g of N-ethyl-2(R)-[1(RS)-(benzyloxycarbamoyl)-2-phthalimidoethyl)-N,4-dimethylvaleraide (8:1 mixture of diastereoisomers), prepared in a manner analogous to that described in Example 13(iii)-(iv), there was obtained 0.083 g of N-ethyl-2(R)-[1 (RS)-(hydroxycarbamoyl)-2-phthalimidoethyl)-N,4-dimethylvaleramide (8:1 mixture of diastereoisomers) in the form of a white solid; nmr (MeOD): 7.85-7.75 (m,4H); 3.95-3.83 (m,1H); 3.75-3.62 (m,1H); 3.4-3.08 (m,10H); 2.95-2.87 (m,1H); 2.83 (m,1H); 1.65-1.55 (m,1H); 1.43-1.33 (m,1H); 1.28-1.13 (m,2H); 1.03 (t,J=6,2H); 0.89 (d,J=6,3H); 0.85 (d,J=6,3H). MS: 390 (M+H)+.

Example 26

In a manner analogous to that described in Example 13, from 0.1 g of 4-[2(R)-[1(RS)-(benzyloxycarbamoyl)-5-phthalimidopentyl]-4-methylvaleryl]morpholine (5:1 mixture of diastereoisomers), prepared in a manner analogous to that described in Example 1(i)–(ii), there was obtained 0.045 g of 4-[2(R)-[1 (RS)-(hydroxycarbamoyl)-5-phthalimidopentyl]-4-methylvaleryl]morpholine (3:1 mixture of diastereoisomers) as a cream colored solid; nmr (MeOD): 7.85-7.75 (m,4H); 3.8-3.49 (m,12H); 3.15 (d,t,1H,J=14,3); 2.18 (dt,1H,J=12,3); 1.68-1.5 (m,4H); 1.38-1.05 (m,5H); 0.86-0.82 (m,6H). MS: 460 (M+H)+.

Example 27

In a manner analogous to that described in Example 13, from 1.06g of N-phenyl-2(R)-[1(R or S)-(benzyloxycarbamoyl)-2-phthalimidoethyl]-N,4-dimethylvaleramide there was obtained, after purification by flash chromatography using 2% methanol in dichloromethane for the elution, 0.65 g of N-phenyl-2(R)-[1(R or S)-(hydroxycarbamoyl)-2-phthalimidoethyl]-N,4-dimethylvaleramide as a white foam; nmr (MeOD): 7.75-7.68 (m,4H); 7.28-7.17 (m,4H); 7.08-7.04 (m,1H); 3.77 (dd,1H,J=14,8); 3.69 (dd,1H,J=14,7); 3.14 (s,3H); 2.78-2.65 (m,2H); 1.62-1.55 (m,1H); 1.42-1.32 (m,1H); 1.25-1.18 (m,1H); 0.7 (d,3H,J=7); 0.54 (d,3H,J=7); MS: 438 (M+H)+.

The starting material was prepared as follows:

(i) A solution of 1.49g 2(R)-[1(R or S)-(tert.butoxycarbonyl)-2-phthalimidoethyl]-4-methylvaleric acid (6:1 mixture of diastereoisomer 1 and diastereoisomer 2) in 20 ml of toluene was cooled to −10° C. A few drops of N,N-dimethylformamide were added, followed by 0.34 ml of oxalyl chloride. The mixture was stirred at −10° C. for 1 hour and then the solvent was evaporated under a high vacuum at 10° C. The residue was redissolved in 10 ml of dichloromethane and cooled to 0° C. 0.5 ml of triethylamine was added, followed by 0.4 ml of N-methylaniline. The mixture was stirred for 1 hour at 0° C. and allowed to warm to room temperature overnight. The solvent was evaporated and the residue was redissolved in 50 ml of ethyl acetate and washed successively with 5% sodium bicarbonate solution, 2N hydrochloric acid and saturated brine solution. The organic phase was dried over anhydrous magnesium sulfate and evaporated to give an orange oil. Purification by flash chromatography on silica gel using 3:1 hexane/ethyl acetate for the elution gave 1.23g of N-phenyl-2(R)-[1(R or S)-(tert-butoxy-carbonyl)-2-phthalimidoethyl]-N,4-dimethylvaleramide (diastereoisomer 1) as a pale yellow oil.; nmr (CDCl3) 7.83-7.78 (m,2H); 7.73-7.68 (m,2H); 7.32-7.05 (m,5H); 4.0 (dd,1H,J=13,9); 3.74 (dd,1H,J=14,6); 3.26 (s,3H); 3.03-2.96 (m,1H); 2.83-2.76 (m,1H); 1.78-1.68 (m,1H); 1.57-1.46 (m,1H); 1.1 (s,9H); 0.87 (d,3H,J=7); 0.65 (d,3H,J=7). MS: 479 (M+H)+.

(ii) In a manner analogous to Example 13 (iv) from 1.23 g of N-phenyl-2(R)-[1(R or S)-(tertbutoxycarbonyl)-2-phthalimidoethyl]-N4-dimethylvaleramide, there were obtained, after flash chromatography using 2% methanol in dichloromethane for the elution, 1.06g of N-phenyl-2(R)-[1(R or S)-(benzyloxycarbamoyl)-2-phthalimidoethyl]-N,4-dimethylvaleramide as a white foam; nmr (CDCl3) 7.8-7.74 (m,4H); 7.45-7.28 (m,6H); 7.04-6.85 (m,4H); 4.96 (d,1H,J=10); 4.89 (d,1H,J=11); 3.95 (dd,1H,J=14,6); 3.72 (dd,1H,J=14,9); 3.17 (s,3H); 3.05-2.98 (m,1H); 2.64-2.58 (m,1H); 1.68-1.6 (m,1H); 1.49-1.32 (m,2H); 0.79 (d,3H,J=6); 0.66 (d,3H,J=6). MS: 528 (M+H)+.

Example 28

In a manner analogous to that described in the first paragraph of Example 13, from 0.31 g of 1-[2(R)-[1(R or S)-(benzyloxycarbamoyl)-2-phthalimidoethyl]-4-methylvaleryl]-2(R)-pyrrolidinemethanol (diastereoisomer 1) there was obtained, after flash chromatography on silica gel using dichloromethane/methanol (15:1) for the elution and crystallization from ethyl acetate, 0.07 g of 1-[2(R)-[1(R or S)-(hydroxycarbamoyl)-2-phthalimidoethyl]-4-methylvaleryl]-2(R)-pyrrolidinemethanol (diastereoisomer 1) in the form of a white solid; nmr (MeOD): 7.86-7.74 (m, 4H); 4.20-4.10 (m, 1H); 4.05-3.97 (m, 1H); 3.81-3.57 (n, 5H); 3.10-3.02 (m, 1H); 2.84-2.76 (m, 1H); 2.14-1.87 (m, 4H); 1.73-1.63 (m, 1H); 1.50-1.35 (m, 1H); 1.24-1.14 (m, 1H); 0.94-0.84 (m, 6H); MS: 432 (M+H)+.

The starting material was prepared as follows:

In a manner analogous to that described in the second paragraph of Example 9, from 0.41 g of 1-[2(R)-[1(R or S)-(tert.butoxycarbonyl)-2-phthalimidoethyl]-4-methylvaleryl]-2(R)-pyrrolidinemethanol (diastereoisomer 1), prepared in a manner analogous to that described in Example 1(i), there was obtained 0.31 g of 1-[2(R)-[1(R or S)-carboxy-2-phthalimido-ethyl]-4-methylvaleryl]-2(R)-pyrrolidinemethanol (diastereoisomer 1) in the form of a pale brown foam which was used without further purification.

Example 29

In a manner analogous to that described in the first paragraph of Example 13, from 0.2 g of benzyl hexahydro-2-[2(R)-[1(R or S)-(benzyloxycarbamoyl)-2-phthalimidoethyl]-4-methylvaleryl]-3(S)-(methylcarbamoyl)1-pyridazinecarboxylate (diastereoisomer 1) there was obtained, after flash chromatography on silica gel using dichloromethane/methanol (20:1) for the elution, 0.044 g of hexahydro-2-[2(R)-[1 (R or S)-(hydroxycarbamoyl)-2-phthalimidoethyl]-4-methylvaleryl]-N-methyl-3(S)-pyridazinecarboxamide (diastereoisomer 1) in the form of a white Solid; nmr (MeOD): 7.83-7.69 (m, 4H); 5.06 (m, 1H); 3.99 (dd, 1H, J=14,9); 3.57 (dd, 1H, J=14,5); 3.04-2.95 (m, 1H); 2.86-2.74 (m, 2H); 2.70 (s, 3H); 2.07-1.86 (m, 2H); 1.68-1.35 (m, 5H); 1.18-1.10 (m, 1H); 0.88 (d, 3H, J=5.5); 0.80 (d, 3H, J=6.0); MS: 474 (M+H)+.

The starting material was prepared as follows:

(i) In a manner analogous to that described in Example 27(i), from 1.02 g of 2(R)-[1(R or S)-(tert.butoxycarbonyl)-2-phthal-imidoethyl]-4-methylvaleric acid (6:1 mixture of diastereoisomer 1 and diastereoisomer 2) and 0.7 g of hexahydro-1-(benzyloxcarbonyl)-(3S)-pyridazinecarboxylic acid, there was obtained, after chromatography on silica gel using ether/hexane (1:4) followed by ethyl acetate for the elution, 0.6 g of hexahydro-1-(benzyloxycarbonyl)-2-[2(R)-[1(R or S)-(tert.butoxycarbon yl)-2-phthalimidoethyl]-4-methylvaleryl]-3(S)-pyridazinecarboxylic acid in the form of a colorless gum.

(ii) A solution of 0.6 g of hexahydro-1-(benzyloxycarbonyl)-2-[2(R)-[1(R or S)-(tert.butoxycarbonyl)-2-phthalimidoethyl]-4-methylvaleryl]-3(S)-pyridazinecarboxylic acid in 5 ml of dimethylformamide was cooled to 0° C. and 0.27 g of 1-hydroxybenzotriazole and 0.36 g of 1-ethyl-3-(3dimethylaminopropyl)carbodiimide hydrochloricle were added. After 40 minutes, 0.4 ml of a 40% aqueous solution of methylamine was added and the mixture was stirred for 2.5 hours. The solvent was evaporated and the residue was treated with 20 ml of 5% aqueous sodium hydrogen carbonate solution. The product was extracted with ethyl acetate and the extract was washed with 5% citric acid and aqueous sodium chloride solution. After drying over anhydrous magnesium sulfate, the solvent was evaporated to give 0.638 g of a colorless gum which was purified by flash chromatography using ether/hexane (3:1) for the elution. There was obtained 0.467 g of benzyl hexahydro-2-[2(R)-[1(R or S)-(tert.butoxycarbonyl)-2-phthalimidoethYl]-4-methylvaleryl]-3(S)-(methylcarbamoyl)-1-pyridazinecarboxylate in the form of a colorless gum.

(iii) In a manner analogous to Example 13(iv) from 0.23 g of benzyl hexahydro-2-[2(R)-[1(R or S)-(tert.butoxycarbonyl)-2-phthalimidoethyl]-4-methylvaleryl]-3(S)-( methylcarbamoyl)-1-pyridazinecarboxylate, there was obtained 0.2 g of benzyl hexahydro-2-[2(R)-[1(R or S)-(benzyloxycarbamoyl)-2-phthalimidoethyl]-4-methylvaleryl]-3(S)-( methylcarbamoyl)-1-pyridazinecarboxylate in the form of a white solid.

Example 30

In a manner analogous to that described in the first paragraph of Example 1 and part (ii) of Example 1, from 0.273 of benzyl hexahydro-2-[2(R)-[1(R or S)-(tert.butoxycarbonyl)-2-phthalimidoethyl]-4-methylvaleryl]-3(S)-(msthylcarbamoyl)-1-pyridazinecarboxylate, there was obtained 0.12 g of benzyl hexahydro-2-[2(R)-(R or S)-(hydroxycarbamoyl)-2-phthalimidoethyl]-4-methylvaleryl]-3(S)-(methylcarbamoyl)-1-pyridazinecarboxylate in the form of a white solid; MS: 608 (M+H)+.

Examale 31

In a manner analogous to that described in the first paragraph of Example 13, from 0.185g of 1-[2(R)-[1(R or S)-(benzyloxycarbamoyl)-2-phthalimidoethyl]-4-methylvaleryl]-N-methyl-2(S)-piperidinecarboxamide, there was obtained, after purification by flash chromatography on silica gel using dichloromethane/methanol (16:1) for the elution, 0.06 mg of 1[2(R)-[1(R or S)-(hydroxycarbamoyl)-2-phthalimidoethyl]-4-methylvaleryl]-N-methyl-2(S)-piperidinecarboxamide (diastereoisomer 1) in the form of a white solid; MS: 473 (M+H)+.

Example 32

In a manner analogous to that described in the first paragraph of Example 1, from 0.22 g of 1-[2(R)-[1(R or S)-carboxy-2-phthalimidoethyl]-4-methylvaleryl]-4-methoxypiperidine (diasteroisomer 1), prepared in a manner analogous to that described in Example 1 (i)--(ii), there was obtained 0.108g of 1-[2(R)-[1(R or S)-(hydroxycarbamoyl)-2-phthalimidoethyl]-4-methylvaleryl]-4-methoxypiperidine (diasteroisomer 1) in the form of a white solid; nmr (MeOD): 7.86-7.74 (m, 4H); 4.05-3.83 (m, 2.5H); 3.70-3.44 (m, 3.5H); 3.41-3.27 (m, 4.5H); 3.10-3.01 (m, 0.5H); 2.97-2.90 (m, 1H); 2.10-2.00 (m, 0.5H); 1.94-1.84 (m, 1H); 1.80-1.68 (m, 1H); 1.66-1.31 (m, 3.5H); 1.21-1.13 (m, 1H); 0.92-0.82 (m, 6H); MS: 446 (M+H)+.

Example 33

In a manner analogous to that described in the first paragraph of Example 1, from 0.44 g of 1-[2(R)-[1(R or S)-carboxy-2-phthalimidoethyl]-4-methylvaleryl]-4-piperidinone, prepared in a manner analogous to that described in Example 1 (ii)–(iii), there was obtained 0.157 g of 1-[2(R)-[1(R or S)-(hydroxycarbamoyl)-2-phthalimidoethyl]-4-methylvaleryl]-4-piperidinone oxime (diastereoisomer 1) in the form of a white solid; nmr (MeOD): 7.86-7.75 (m, 4H); 3.92-3.76 (m, 3H); 3.72-3.58 (m, 2H); 3.38-2.82 (m, 3H); 2.71-2.25 (m, 4H); 1.66-1.57 (m, 1H); 1.48-1.34 (m, 1H); 1.26-1.17 (m, 1H); 0.92-0.82 (m, 6H); MS: 445 (M+H)+.

Example 34

In a manner analogous to that described in the first paragraph of Example 13, from 0.32 g of N-[2(R)-[1(R or S)-(benzyloxycarbamoyl)-2-phthalimidoethyl]-4-methylvaleryl]-L-proline methyl ester (diastereoisomer 1), prepared in a manner analogous is that described in Example 13 (iii)–(iv), there was obtained 0.13g of N-[2(R)-[1(R or S)-(hydroxycarbamoyl)-2-phthalimidoethyl]-4-methylvaleryl]-L-Proline methyl ester (diasteroisomer 1) in the form of a white solid; nmr (MeOD): 7.86-7.77 (m, 4H); 3.95-3.84 (m, 2H); 3.78 (d, 2H, J=8); 3.69-3.61 (m, 1H); 3.60 (s, 3H); 3.11-3.04 (m, 1H); 3.00-2.92 (m, 1H); 2.21-2.12 (m, 1H); 2.10-1.95 (m, 2H); 1.90-1.82 (m, 1H); 1.74-1.63 (m, 1H); 1.60-1.52 (m, 1H); 1.22-1.14 (m, 1H); 0.94 (d, 3H, J=6); 0.86 (d, 3H, J=6); MS: 460 (M+H)+.

Example 35

In a manner analogous to that described in the first paragraph of Example 13, from 1.116g of 1-[2(R)-[1(R or S)-(benzyloxycarbamoyl)-2-(3,4,4-trimethyl-2,5-dioxo-1 -imidazolidinyl)ethyl]-4-methylvaleryl]-4-piperidinol (diastereoisomer 1), prepared in a manner analogous to that described in Example 14 (i)–(ii), there was obtained 0.785 g of 1-[2(R)-[1(R or S)-(hydroxycarbamoyl)-2-(3,4,4-trimethyl-2,5-dioxo-1-imidazolidinyl) ethyl]-4-methylvaleryl]-4-piperidinol (diastereoisomer 1) in the form of a white solid; nmr (MeOD): 4.24-4.01 (m, 2H); 3.93-3.81 (m, 1H); 3.78-3.64 (m, 1H); 3.52-3.22 (m, 4H); 3.10-2.81 (m, 4H); 2.02-1.77 (m,2H); 1.67-1.26 (m, 10H); 1.19-1.09 (m, 1H); 0.93-0.82 (m, 6H); MS: 427 (M+H)+.

Example 36

In a manner analogous to that described in the first paragraph of Example 1, from 1.55g of 1-[2(R)-1(R-S)-carboxy-2-(tetrahydro-2-methyl-3,5-dioxo-1,2,4-oxadiazol-4-yl) ethyl]-4-methylvaleryl]-4-piperidine (diastereoisomer 1 ) there was obtained 0.572 g of 1-[2(R)-1(R-S)-(hydroxycarbamoyl)-2-(tetrahydro-2-methyl-3,5-dioxo-1,2,4-oxadiazol-4-yl) ethyl]-4-methylvaleryl]-

4-piperidine (diastereoisomer 1) in the form of a white solid; nmr (MeOD): 3.70-3.46 (m, 4H); 3.42-3.29 (m, 2H); 3.25-3.15 (m, 4H); 2.89-2.76 (m, 1H); 1.68-1.27 (m, 8H); 1.27-1.04 (m, 1H); 0.83-0.76 (m, 6H); MS: 385 (M+H)+.

The starting material was prepared as follows: (i) In a manner analogous to that described in Example 18(i)—(ii), from 4.76g of 1,2-dibenzyl 1-tert.butyl 4-methyl-1,1,2 (R)-pentanetricarboxylate and 2.05g of 4-bromomethyl-2-tetrahydro-2-methyl-3,5-dioxo-1,2,4-oxadiazole, there was obtained 1.55g of 1-[2(R)-1(R or S)-carboxy-2-(tetrahydro-2-methyl-3,5-dioxo-1,2,4-oxadiazol -4-yl)ethyl]-4-methylvaleryl]-4- piperidine (diastereoisomer 1) in the form of a gum which is used without further purification.

Example 37

In a manner analogous to that described in the first paragraph of Example 13, from 0.184g of 1-[2(R)-[1(R or S)-(benzyloxycarbamoyl)-2-(3-methyl-2,4,5-trioxo-1-imidazolidinyl)ethyl]-4-methylvaleryl]-4-piperidinol (diastereoisomer 1), prepared in a manner analogous to that described in Example 14(i)–(ii) from 1,2-dibenzyl 1-tert.butyl 4-methyl-1,1,2 (R)-pentanetricarboxylate and 1-bromomethyl-3-methyl-2,4,5-trioxo-1-imidazole, there was obtained 0.08 g of 1-[2(R)-[1(R or S)-(hydroxycarbamoyl)-2-(3-methyl-2,4,5-trioxo-1-imidazolidinyl) ethyl]-4-methylvaleryl]-4-piperidinol (diastereoisomer 1) in the form of a white solid; nmr (MeOD) 4.20-3.95 (m, 2H); 3.93-3.75 (m, 2H); 3.57-2.97 (m, 7H); 2.90-2.81 (m, 1H); 2.02-1.76 (m, 2H); 1.66-1.29 (m, 4H); 1.20-1.12 (m, s 1H); 0.91-0.82 (m, 6H); MS: 413 (M+H)+.

Example 38

In a manner analogous to that described in the first paragraph of Example 13, from 0.261 g of 1-[2(R)-[1(R or S)-(benzyloxycarbamoyl)-2-( 2,5-dioxo-3-phenyl-1-imidazolidinyl)ethyl]-4-methylvaleryl]-4-piperidinol (diastereoisomer 1), prepared in a manner analogous to that described in Example 14(i)–(ii), there was obtained 0.169 g of 1-[2(R)-[1(R or S)-(hydroxycarbamoyl)-2-(2,5-dioxo-3-phenyl-1-imidazolidinyl)ethyl]-4-methyl-valerYl]-4-piperidinol (diastereoisomer 1) in the form of a white solid; nmr (MeOD): 7.60-7.55 (m, 2H); 7.35-7.29 (m, 2H); 7.12-7.05 (m, 1H); 4.37- 4.24 (m, 2H); 4.19-3.92 (m, 2H); 3.89-3.66 (m, 2H); 3.54-2.84 (m, H); 1.99-1.71 (m, 2H); 1.64-1.23 (m, 4H); 1.17-1.08 (m, 1H); 0.88-0.78 (m, 6H); MS: 461 (M+H)+.

Example 39

In a manner analogous to that described in the first paragraph of Example 13, from 0.146g of 4-[2(R)-[1(R or S)-(benzyloxycarbamoyl)-2-( 3-methyl-2,4,5-trioxo-1-imidazolidinyl) ethyl]-4-methylvaleryl]morpholine (diastereoisomer 1), prepared in a manner analogous to that described in Example 14(i)–(ii), there was obtained 0.085 g of 4-[2(R)-[1 (R or S)-(hydroxycarbamoyl)-2-(3-methyl-2,4,5-trioxo-1-imidazolidinyl) ethyl]-4-methyl-valeryl]morpholine (diastereoisomer 1) in the form of a white sollid; nmr (MeOD): 3.86-3.54 (m. 10H); 3.28-3.20 (m, 1H); 3.08 (s, 3H); 2.91-2.82 (m, 1H); 1.66-1.57 (m, 1H); 1.48-1.36 (m, 1H); 1.23-1.15 (m, 1H); 0.89-0.84 (m, 6H); MS: 399 (M+H)+.

Example 40

In a manner analogous to that described in the first paragraph of Example 13, from 0.363 g of N2-[2(R)-[1(R or S)-(benzyloxycarbamoyl)-2-(3,4,4-trimethyl-2,5-dioxo-1-imidazolidinyl)ethyl]-4-methylvaleryl]-$N^1$-methyl-L-prolinamide (diastereoisomer 1), prepared in a manner analogous to that described in Example 14(i)—(ii), there was obtained 0.234 g of $N^2$-[2(R)-[1(R or S)-(hydroxycarbamoyl)-2-(3,4,4-trimethyl-2,5-dioxo-1-imidazolidinyl) ethyl]-4-methylvaleryl]-$N^1$-methyl-L-prolinamide (diastereoisomer 1) in the form of a white solid; nmr (MeOD): 4.35-4.29 (m, 1H); 3.92-3.83 (m, 1H); 3.74-3.58 (m, 2H); 3.47-3.41 (m, 1H); 3.10-3.01 (m, 1H); 2.88-2.75 (m, 4H); 2.59 (s, 3H); 2.26-1.84 (m, 4H); 1.74-1.55 (m, 2H); 1.34 (s, 3H); 1.32 (s, 3H); 1.18-1.11 (m, 1H); 0.92 (d, 3H, J=5.5); 0.86 (d, 3H, J=6); MS: 454 (M+H)+.

Example 41

In a manner analogous to that described in the first paragraph of Example 13, from 0.3 g of 1-[2(R)-[1(R or S)-(benzyloxycarbamoyl)-2-(2-oxo-1-pyrrolidinyl)ethyl]-4-methylvaleryl]-4-piperidinol (diastereoisomer 1), prepared in a manner analogous to that described in Example 14(i)–(ii), there was obtained 0.116 g of 1-[2(R)-[1(R or S)-(hydroxycarbamoyl)-2-(2-oxo-1-pyrrolidinyl) ethyl]-4-methylvaleryl]-4-piperidinol (diastereoisomer 1) in the form of a white solid; nmr (MeOD): 4.16-3.91 (m, 2H); 3.84-3.73 (m, 1H); 3.43-2.97 (m, 7H); 2.56-2.45 (m, 1H); 2.27-2.18 (m, 2H); 1.96-1.70 (m, 4H); 1.61-1.19 (m, 4H); 1.11-1.01 (m, 1H) 0.84-0.72 (m, 6H); MS: 370 (M+H)+.

Example 42

In a manner analogous to that described in the first paragraph of Example 13, from 0.16g of 1-[2(R)-1(R or S)-(benzyloxycarbamoyl)-2-(2,5-dioxo-1 -pyrrolidinyl)ethyl]-4-methylvaleryl]-4-piperidinol (diastereoisomer 1), prepared in a manner analogous to that described in Example 14(i)–(ii), there was obtained 0.048 g of 1-[2(R)-1(R or S)-(hydroxycarbamoyl)-2-(2,5-dioxo-1-pyrrolidinyl) ethyl]-4-methylvaleryl]-4piperidinol (diastereoisomerl) in the form of a white solid; nmr (MeOD): 4.25-4.01 (m, 2H); 3.94-3.80 (m, 1H); 3.78-3.63 (m, 1H); 3.52-3.02 (m, 4H); 2.82-2.73 (m, 1H); 2.63 (d, 4H, J=6); 2.04-1.76 (m, 2H); 1.64-1.27 (m, 4H); 1.18-1.09 (m, 1H); 0.92-0.80 (m, 6H); MS: 384 (M+H)+.

Example 43

In a manner analogous to that described in the first paragraph of Example 13, from 0.43 g of 1-[2(R)-[1(R or S)-(benzyloxycarbamoyl)-2-(3-methyl-2,5-dioxo-1-imidazolidinyl)ethyl]-4-methylvaleryl]-4-piperidinol (diasteroisomer 1), prepared in a manner analogous to that described in Example 14(i)–(ii), there was obtained 0.158 g of 1-[2(R)-[1 (R or S)-(hydroxycarbamoyl)-2-(3-methyl-2,5-dioxo-1-imidazolidinyl) ethyl]-4-methyl-valeryl]-4-piperidinol (diastereoisomer 1) in the form of a white solid; nmr (MeOD): 4.25-3.97 (m, 2H); 3.93-3.79 (m, 2H); 3.74-3.61 (m, 1H); 3.52-2.97 (m, 4H); 2.93-2.80 (m, 4H); 2.02-1.76 (m, 2H); 1.67-1.27 (m, 4H); 1.19-1.10 (m, 1H); 0.91-0.80 (m, 6H); MS: 399 (M+H)+.

The Examples which follow illustrate pharmaceutical preparations containing the hydroxamic acid derivatives provided by the invention:

Example A

Tablets containing the following ingredients may be produced in a conventional manner:

| Ingredient | Per Tablet |
| --- | --- |
| Hydroxamic acid derivative | 10.0 mg |
| Lactose | 125.0 mg |
| Corn starch | 75.0 mg |
| Talc | 4.0 mg |
| Magnesium stearate | 1.0 mg |
| Total weight | 215.0 mg |

Example B

Capsules containing the following ingredients may be produced in a conventional manner:

| Ingredient | Per Capsule |
| --- | --- |
| Hydroxamic acid derivative | 10.0 mg |
| Lactose | 165.0 mg |
| Corn starch | 20.0 mg |
| Talc | 5.0 mg |
| Capsule fill weight | 200.0 mg |

We claim:

1. A method for the control or prevention of degenerative joint diseases which comprises administering to a host requiring such treatment on effective amount of a compound of the formula

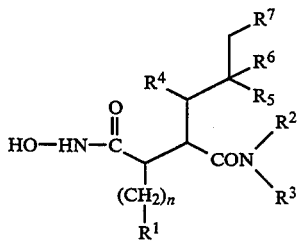

(I)

wherein $R^1$ is a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other C atoms by lower alkyl or oxo and/or on any additional N atom(s) by lower alkyl or aryl;

$R^2$ is lower alkyl and $R^3$ represents lower alkyl or aryl, or $NR^2R^3$ is a saturated 5-, 6- or 7-membered heterocyclic ring which optionally contains —$NR^a$, —(O)—, —S—, —SO— or —$SO_2$— as a ring member and/or which is optionally substituted by hydroxy, lower alkoxy, oxo, ketalized oxo, amino, mono(lower alkyl)amino, di(lower alkyl)amino, carboxy, lower alkoxycarbonyl, hydroxy-methyl, lower alkoxymethyl, carbamoyl, mono(lower alkyl)-carbamoyl, di(lower alkyl)carbamoyl or hydroxyimino;

$R^a$ is hydrogen, lower alkyl, lower alkanoyl, aryl-lower alkanoyl, lower alkoxycarbonyl, aryl-lower alkoxycarbonyl or mono(lower alkyl)carbamoyl;

$R^4$, $R^5$, $R^6$ and $R^7$ each, independently, is hydrogen or methyl, provided that at least two of these symbols are hydrogen; and n stands for 1–4; or a pharmaceutically acceptable salt thereof.

2. A method according to claim 1, wherein $R^1$ is a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other C atoms by lower alkyl or oxo and/or on any additional N atom(s) by lower alkyl; $R^2$ is lower alkyl and $R^3$ is lower alkyl or aryl or $NR^2R^3$ is a saturated 5-, 6- or 7-membered heterocyclic ring which optionally contains —$NR^a$, —O—, —S—, —SO— or —$SO_2$— as a ring member and/or which is optionally substituted by hydroxy, lower alkoxy, oxo, ketalized oxo, amino, mono(lower alkyl)amino, di(lower alkyl)amino, carboxy, lower alkoxycarbonyl, hydroxymethyl, lower alkoxymethyl, carbamoyl, mono(lower alkyl)carbamoyl or di(lower alkyl)carbamoyl; and Ra is hydrogen or lower alkyl.

3. A method according to claim 2, wherein the N-heterocyclic ring $R^1$ optionally contains as additional hetero atom(s) one or two N atoms, one N atom and one O atom or one O atom.

4. A method according to claim 3, wherein $R^1$ is a ring of the formula

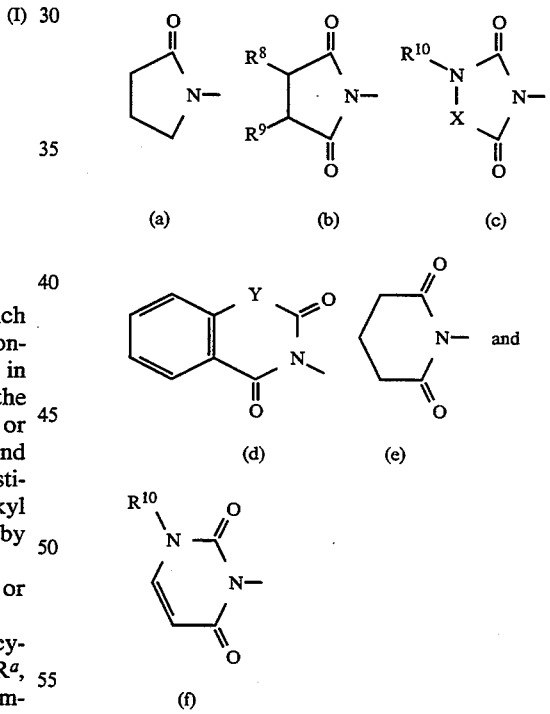

in which $R^8$ and $R^9$ each, independently, is hydrogen or taken together are an additional bond or the remainder of a fused benzene ring;

$R^{10}$ is hydrogen, lower alkyl or aryl;

X is —CO—, —$CH_2$—, —CH(lower alkyl)—, —C(-lower alkyl)$_2$—, —NH—, —N(lower alkyl)— or —O—; and Y is —O—, —NH— or —N(lower alkyl)—.

5. A method according to claim 4, wherein $R^{10}$ is hydrogen or lower alkyl.

6. A method according to claim 5, wherein $R^1$ is a ring of formula (b) or (c).

7. A method according to claim 6, wherein $R^1$ is phthalimido, 1,2-dimethyl-3,5-dioxo-1,2,4-triazolidin-4-yl, 3-methyl-2,5-dioxo-1-imidazolidinyl or 3,4,4-trimethyl-2,5-dioxo-1-imidaxolidinyl.

8. A method according to claim 7, wherein $NR^2R^3$ is a 5-, 6- or 7-membered saturated heterocyclic ring.

9. A method according to claim 8, wherein $NR^2R^3$ is a 6-membered saturated heterocyclic ring.

* * * * *

UNITED STATES PATENT AND TRADEMARK OFFICE
CERTIFICATE OF CORRECTION

PATENT NO. : 5,447,929
DATED : September 5, 1995
INVENTOR(S) : Michael J. Broadhurst, et al It is certified that error appears in the above-indentified patent and that said Letters Patent is hereby corrected as shown below:

Claim 1, Column 27, line 61: "carbarnoyl" should read --- carbamoyl --- .

Claim 2, Column 28, line 12: "N atorn(s)" should read --- N atom(s) --- .

Claim 7, Column 30, line 2: "trimethyl-2,5-dioxo-1-imidaxolidinyl." should read --- trimethyl-2,5-dioxo-1-imidazolidinyl. --- .

Signed and Sealed this

Twenty-eighth Day of November 1995

Attest:

BRUCE LEHMAN

Attesting Officer

Commissioner of Patents and Trademarks